United States Patent [19]

Erion et al.

[11] Patent Number: 5,731,432
[45] Date of Patent: Mar. 24, 1998

[54] INHIBITORS OF ADENOSINE MONOPHOSPHATE DEAMINASE

[75] Inventors: Mark D. Erion, Del Mar; Brett C. Bookser, Solana Beach; Srinivas Rao Kasibhatla, San Diego; Harry E. Gruber, Rancho Santa Fe, all of Calif.

[73] Assignee: Gensia Sicor Inc., San Diego, Calif.

[21] Appl. No.: 192,154

[22] Filed: Feb. 3, 1994

Related U.S. Application Data

[63] Continuation-in-part of Ser. No. 12,841, Feb. 3, 1993.
[51] Int. Cl.⁶ .................................................. C07D 491/04
[52] U.S. Cl. .......................... 540/568; 514/221; 540/554
[58] Field of Search ................... 540/554, 568; 514/221

[56] References Cited

U.S. PATENT DOCUMENTS 4,935,505   6/1990   Townsend et al. ............... 536/24

FOREIGN PATENT DOCUMENTS 0 6012 322 A   6/1994   European Pat. Off. .
89 08658 A      9/1989   WIPO .
94 17809 A      8/1994   WIPO .

OTHER PUBLICATIONS

Danton, et al., "Isolation of Mutant Adenosine Deaminase by Coformycin Affinity Chromatography" *Anal. Biochem.* 159(1):233–239 (1986).

Omura, et al., "Manufacture of Novel Compound OM-3223 as Adenosine Deaminase Inhibitor for Therapeutic Use " *Chem. Abstr.* 107(9), Abract No. 76096 (1987).

Showalter, et al., "Studies Related to the Total Synthesis of Pntostatin: An Efficient, Regiospecific Glycosylation of 6,7-dihydroimidazo[4,5-d][1,2]diazepin-8(3H)-one and Related Homologs" *Tetrahedron Lett.* 22(33):3155–3158 (1981).

*Primary Examiner*—Yogendra N. Gupta
*Attorney, Agent, or Firm*—Lyon & Lyon LLP

[57] ABSTRACT

Novel diazepine derivatives which selectively inhibit adenosine monophosphate deaminase and methods of preparing these compounds are provided. These compounds are useful in treating certain conditions in vivo which may be ameliorated by increased local concentrations of adenosine.

41 Claims, No Drawings

INHIBITORS OF ADENOSINE MONOPHOSPHATE DEAMINASE

RELATED APPLICATIONS

This application is a continuation-in-part of Ser. No. 08/012,841 filed Feb. 3, 1993.

FIELD OF THE INVENTION

This invention relates to adenosine monophosphate deaminase inhibitors and to novel diazepine analogs, specifically to 3-substituted 3,6,7,8-tetrahydroimidazo[4,5-d] diazepine analogs having activity as adenosine monophosphate deaminase inhibitors. The invention also relates to the preparation and use of these and other adenosine monophosphate deaminase inhibitors in the treatment of cardiovascular, and cerebrovascular diseases, central nervous system diseases, seizures, inflammation, sepsis, septic shock, endotoxemia, cancer, malaria and other parasites, AIDS (acquired immune deficiency syndrome), and other diseases and in the treatment of pain.

BACKGROUND AND INTRODUCTION TO THE INVENTION

The present invention is directed to novel compounds which may act to increase local adenosine levels.

Adenosine has been reported to have cardioprotective and neuroprotective properties. However, adenosine has also been reported to exhibit negative inotropic, chronotropic and dromotropic effects and to cause coronary steal by preferentially dilating vessels in nonischemic regions after systemic administration. These side effects limits the therapeutic potential of adenosine and other adenosine receptor agonists. Thus, it would be advantageous to increase adenosine concentrations locally, i.e. at a target site within the target tissue so that the beneficial effects of adenosine could be provided and the toxic systemic effects minimized.

Adenosine monophosphate (AMP) deaminase ("AMP deaminase" or "AMPDA") is a cytosolic enzyme which catalyzes the deamination of AMP to inosine monophosphate (IMP). Adenosine production is reported to be especially enhanced during ischemia when oxygen deprivation leads to adenosine triphosphate (ATP) breakdown and elevated intracellular levels of AMP. Intracellular AMP is catabolized to either adenosine by 5'-nucleotidase or converted to IMP by AMP deaminase. Studies have shown that AMPDA is a major pathway for AMP metabolism in ischemic tissues. Thus inhibition of AMPDA will lead to increased adenosine levels in a site- and event-specific manner.

Adenosine is metabolized either via phosphorylation of the 5'-hydroxyl by adenosine kinase ("AK") to give AMP or via deamination by adenosine deaminase ("ADA") to give inosine. Factors that determine the predominate pathway include local adenosine concentrations, kinetic characteristics of ADA and AK, and ADA versus AK intracellular specific activity. Since physiological adenosine concentrations are <100 nM and since ADA has a 100-fold higher Km for adenosine (Km=~50 µM) relative to that of AK (Km=0.5 µM), ADA may be a significant factor in adenosine metabolism only at high adenosine concentrations. The rapid breakdown of ATP during ischemia leads to elevated local adenosine levels. Consequently, if adenosine levels are raised 100 fold during ischemia, ADA may begin to become important in local adenosine metabolism.

Chronic total inhibition of ADA has been reported to lead to severe immunodeficiency. Children that are genetically deficient in ADA lack T- and B-cell activity and therefore are prone to a wide variety of life-threatening infections and diseases. Irreversible inhibition of ADA by the potent inhibitor, 2'-deoxycoformycin, has been reported to lead to a loss in B- and T-cell function and overall immunodeficiency. Although ADA deficiency and ADA inhibition leads to immunodeficiency, these studies have not found higher plasma adenosine levels.

Gruber, U.S. Pat. No. 4,912,092, discloses (claim 38) "a method for enhancing the extracellular concentration of adenosine in tissue having an undesired region of decreased blood flow comprising the prophylactic administration of an adenosine monophosphate deaminase inhibitor."

Four coformycin analogs have been reported to show activity as AMPDA inhibitors. The 5'-phosphorylated analogs of coformycin and deoxycoformycin have been reported to be potent inhibitors of rabbit muscle AMPDA ($\leq 1$ nM). These compounds, however, are not expected to be useful in vivo since they would not be bioavailable in cells due to the presence of the highly charged phosphate group. Secondly, dephosphorylation in vivo, which is a common and rapid metabolic pathway for other 5'-monophosphate nucleotides and other organophosphates in general would produce coformycin and deoxycoformycin respectively. Coformycin and deoxycoformycin are very potent inhibitors of ADA (<0.2 nM) but are significantly weaker AMPDA inhibitors (1000 nM). Kinetic studies on the inhibition of ADA with coformycin and deoxycoformycin have shown that these compounds are tight binding inhibitors that result in irreversible inhibition of ADA. Consequently, inhibition of AMPDA with these compounds would lead to complete inhibition of ADA.

Other coformycin analogs that have been reported include the aglycon attached to a short oxygenated chain, (acyclocoformycin in Showalter, et al., *J. Med. Chem.* 1983, 26, 1478–1482). No special utility or potential utility was reported for these compounds.

SUMMARY OF THE INVENTION

The present invention is directed towards novel compounds which are potent AMPDA inhibitors. In one aspect, the present invention is directed to certain novel compounds that inhibit AMPDA, to the preparation of these compounds and to the in vitro and in vivo AMPDA inhibitory activity of these compounds. Another aspect of the present invention is directed to the clinical use of AMPDA inhibitors as a method of treatment or prevention of diseases responsive to enhanced local adenosine levels and in diseases responsive to modulation of purine metabolism flux.

Although we do not wish to be bound by this or any particular theory, we believe that the novel adenosine monophosphate deaminase ("AMPDA") inhibitors of the present invention will be useful in enhancing local concentrations of adenosine in tissues which may benefit from increased extracellular adenosine levels in a site- and event-specific manner (Gruber, U.S. Pat. No. 4,912,092). In one aspect, we believe that these AMPDA inhibitors will be useful in increasing adenosine levels in ischemic tissues. We believe ischemic tissues would have higher AMP levels relative to nonischemic tissues due to net ATP breakdown. Inhibition of AMPDA would result in higher adenosine levels in the ischemic tissue without a global effect since AMP levels would not be increased in normal tissues. For example, these compounds may be useful in increasing adenosine production in ischemic cardiac tissue and therefore, increasing local adenosine levels and providing protection against damage.

Gruber, U.S. Pat. No. 4,912,092, described the use of AMP deaminase inhibitors for treating diseases benefited by increased extracellular adenosine. AICA riboside which after phosphorylation to ZMP is able to inhibit AMP deaminase. ZMP, however, is rapidly cleared by a variety of enzymes including nucleotidase and cannot penetrate the cell membrane. We have demonstrated the ability of cell penetrable molecules to directly inhibit AMP deaminase, some of which are also capable of inhibiting adenosine deaminase. These cell penetrable molecules and prodrugs thereof, which are not cleaved by nucleotidase, are active in a variety of models of human diseases some of which are described herein. Direct enzyme inhibitors of the present invention have the advantage of not requiring metabolic energy (such as ATP and PRPP) as is required by molecules that undergo phosphoribosylation or phosphorylation. This advantage is especially important in cells undergoing net ATP depletion due to a lack of oxygen or nutrients as occurs during ischemia including central nervous system or cardiac ischemia. Furthermore, these molecules are specific AMP deaminase and optionally mixed AMP and adenosine deaminase inhibitors. That is, they do not inhibit adenosine kinase, adenosine transport or bind adenosine receptors in the concentration ranges where they almost completely inhibit AMP deaminase. Without inhibiting other enzymes, they are less likely to cause undesired side effects.

Among other factors, the present invention is based on our finding that the novel compounds of the present invention are useful as AMP deaminase inhibitors and act to elevate and prolong extracellular adenosine levels and thereby enhance the pharmacological benefits of adenosine locally. These compounds are especially useful for the treatment of conditions and disorders responsive to the inhibition of AMP deaminase, particularly cardiovascular disorders, including cardiac arrhythmias and especially conditions related to ischemia such as myocardial infarction, angina (stable and unstable), percutaneous transluminal coronary angiography (PTCA), congestive heart failure, atherosclerosis, and other thrombotic and embolic disorders.

The compounds are also useful in treating or preventing disorders such as stroke, neurologic disorders such as pain, seizure, insomnia, anxiety, or psychosis, and other conditions benefited by enhanced adenosine levels (at a selected locus) including inflammation, arthritis, autoimmune disease, ulcers and irritable bowel syndrome. Further, the compounds of the present invention are especially useful in the treatment or prevention of septic shock, sepsis, SIRS (SIRS is defined in Critical Care Medicine, vol 20, page 864–874, 1992, as a condition with no other apparent cause characterized by two or more of the following states: 1) body temperature >38° C. or less than 36° C.; 2 heart rate >90 beats/minute; 3) tachypnea with >20 breaths/minute or $pCO_2$<32 torr; or 4) white blood cell count >12,000 or <4,000 cells/mL or >10% immature neutrophils.), pancreatitis, burns and endotoxemia. In addition these compounds are useful as muscle relaxants, in inducing sleep and in treating anxiety.

The present invention is further directed to the prophylactic and affirmative treatment of pain. AMP deaminase and mixed AMP and adenosine deaminase inhibitors are useful in the treatment of acute and chronic pain apparently by their ability to raise adenosine concentrations and down-regulate pain transmission in the spinal cord. For example, AMP deaminase inhibitors are useful in the treatment or prevention of acute and chronic pain.

Accordingly, the present invention is directed to novel compounds that may be used clinically to treat or prevent medical conditions where an increased local adenosine concentration or where changes of purine metabolism is beneficial, such as cancer, gout, AIDS, or infection with malaria or other parasites.

Further, in one embodiment the present invention is directed at compounds which are specific inhibitors of AMPDA and which show little or no interaction with other enzymes. In another embodiment, the present invention is directed to compounds which are selective inhibitors for both AMPDA and adenosine deaminase.

These compounds comprise novel 3-substituted-[3,6,7,8-tetrahydroimidazo[4,5-d]1,3]diazepine derivatives as specified below in formula 1. Also included in the scope of the present invention are prodrugs of the compounds of formula 1.

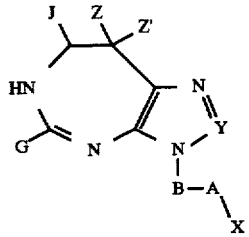

Formula 1

Since these compounds may have asymmetric centers, the present invention is directed not only to racemic mixtures of these compounds, but to individual stereoisomers. The present invention also includes pharmaceutically acceptable and/or useful salts of the compounds of formula 1, including acid addition salts and basic salts. These salts may be formed by the addition of hydrobromic, hydrochloric, sulfuric and like acids or by the addition of carboxylic or sulfonic and like acids. The basic salts may be formed by treatment with a suitable base such as sodium or potassium hydroxide. Also included in the scope of the present invention are prodrugs of the compounds of formula 1.

DEFINITIONS

In accordance with the present invention and as used herein, the following terms are defined with the following meanings, unless explicitly stated otherwise.

The term "aryl" refers aromatic groups which have at least one ring having a conjugated pi electron system and includes carbocyclic aryl, heterocyclic aryl and biaryl groups, all of which may be optionally substituted. Carbocyclic aryl groups are groups wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl groups are groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

The term "biaryl" represents aryl groups containing more than one aromatic ring including both fused ring systems and aryl groups substituted with other aryl groups.

The term "alicyclic" means compounds which combine the properties of aliphatic and cyclic compounds and include but are not limited to aromatic, cycloalkyl and bridged cycloalkyl compounds.

The term "optionally substituted" or "substituted" includes groups substituted by one to four substituents, independently selected from lower alkyl, lower aryl, lower aryloxy, aralkyl, perhaloakloxy, aralkoxy, heteroaryl, heteroaryloxy, heteroarylalkyl, heteroaralkoxy, azido, amino, guanidino, tetrazolo, 3H-1,2,3,5-oxythiodiazolo, thiazolidine- 2,4-diono, oxazolidin-2,4-diono, halogen, hydroxy, lower alkoxy, lower alkylthio, carboxyalkyl, carboxyl, carboxamido, carboxamidoalkylaryl, carboxamidoaryl, aminocarboxamidoalkyl, cyano, and lower perhaloalkyl.

The term "aralkyl" refers to an alkyl group substituted with an aryl group. Suitable aralkyl groups include benzyl, picolyl, and the like, and may be optionally substituted.

The term "lower" referred to herein in connection with organic radicals or compounds respectively defines such as with up to and including 10, preferably up to and including and advantageously one or two carbon atoms. Such groups may be straight chain or branched.

The terms "arylamino" (a), and "aralkylamino" (b), respectively, refer to the group —NRR' wherein respectively, (a) R is aryl and R' is hydrogen or aryl, and (b) R is aralkyl and R' is hydrogen or aralkyl.

The term "alkylamino" refers to —NRR' where R and R' are independently selected from hydrogen or lower alkyl.

The term "carboxamide" or "carboxamido" refers to —$CONR_2$ where each R is independently hydrogen or alkyl.

The term "alkyl" refers to saturated aliphatic groups including straight-chain, branched chain and cyclic groups.

The term "alkenyl" refers to unsaturated groups which contain at least one carbon-carbon double bond and includes straight-chain, branched-chain and cyclic groups.

The term "alkynyl" refers to unsaturated groups which contain at least one carbon-carbon triple bond and includes straight-chain, branched-chain and cyclic groups.

The term "alkylene" refers to a divalent straight chain or branched chain saturated aliphatic radical.

The term "acyloxy" refers to the ester group —O—C(O)R.

The term "thioacyloxy" refers to the thioester group —S—C(O)R.

The term "alkylenylaryl" refers to an alkylene group substituted with an aryl group. "Lower alkylenylaryl" refers to such groups where alkylene is lower alkylene.

The term "alkylenylamino" refers to the group -alk-NH— wherein alk is an alkylene group.

The term "alkylenylaminoalkylene" refers to the group -alk-NH-alk- wherein each alk is an independently selected alkylene. "Lower alkylenylaminoalkylene" refers to groups where each alkylene group is lower alkylene.

The term "alkylenylaminoaryl" refers to an alkylene group substituted with an arylamino group. In "lower alkenylaminoaryl", the alkylene group is lower alkylene.

The term "alkylenyloxyaryl" refers to an alkylene group substituted with an aryloxy group. In "lower alkylenyloxyaryl", the alkylene group is lower alkylene.

The term "alkylenylacylamino" refers to the group -alk—NH—(COR)— wherein alk is alkylene and R is lower alkyl. In "lower alkylenylacylamino", the alkylene group is lower alkylene.

The term "alkylenyloxyalkylenylaryl" refers to an alkylene group substituted with an aralkyloxy group. "Lower alkylenyloxyalkylenylaryl" refers to such groups where the alkylene group is lower alkylene.

The term "alkylenylacylaminoalkylene refers to the group -alk-NH—(COR)-alk- where each alk is an independently selected alkylene group. In "lower alkylenylacylaminoalkylene" the alkylene groups are lower alkylene.

The term "alkenyloxy" refers to the group -alk-O— wherein alk is an alkylene group.

The term "alkoxyalkyl" refers to the group -alk-O-alk- wherein each alk is an independently selected alkylene group. In "lower alkoxyalkyl", each alkylene is lower alkylene.

The term "alkylenethio" refers to the group -alk-S— wherein alk is alkylene group.

The term "alkylthioalkyl" refers to the group -alk-S-alk- wherein each alk is an independently selected alkylene group. In "lower alkylthioalkyl" each alkylene is lower alkylene.

The term "alkylcarboxamidoalkyl" refers to the group -alk-C(O)N(R)-alk- wherein each alk is an independently selected alkylene group and R is lower alkyl. In "lower alkylcarboxamidoalkyl", each alkylene is lower alkylene.

The term "alkylcarboxamidoalkylaryl" refers to the group -$alk_1$-C(O)—NH-$alk_2$(Ar)— wherein $alk_1$ and $alk_2$ are independently selected alkylene groups and $alk_2$ is substituted with an aryl group, Ar. In "lower alkylcarboxamidoalkylaryl", each alkylene is lower alkylene.

The term "heteroalicyclic" refers to an alicyclic group having 1 to 5 heteroatoms selected from nitrogen, sulfur, phosphorus and oxygen.

The term "aminocarboxamidoalkyl" refers to the group —NH—C(O)—N(R—R wherein each R is an independently selected alkyl group. "Lower aminocaboxamidoalkyl" refers to such groups wherein each R is lower alkyl. The term "heteroarylalkyl" refers to an alkyl group substituted with a heteroaryl group.

The term "CONH-amino acid" refers to a carbonyl bound to the N-terminus of an amino acid.

The term "coformycin aglycone" refers to 3',6',7',8'-tetrahydroimidazo [4',5'-d][1',3']diazepin-8-ol.

The term "prodrug" as used herein refers to any compound that when administered to a biological system generates the "drug" substance either as a result of spontaneous chemical reaction(s) or by enzyme catalyzed or metabolic reaction(s). Reference is made to various prodrugs such as acyl esters, carbonates, and urethanes, included herein. The groups illustrated are exemplary, not exhaustive and one skilled in the art could prepare other known varieties of prodrugs. Such prodrugs of the compounds of formula 1, fall within the scope of the present invention.

The term "pharmaceutically acceptable salt" includes salts of compounds of formula 1 derived from the combination of a compound of this invention and an organic or inorganic acid or base. The compounds of formula 1 are useful in both free base and salt form. In practice the use of salt form amounts to use of base form; both forms are within the scope of the present invention.

DETAILED DESCRIPTION OF THE INVENTION

Novel Diazepine Compounds

Preferred compounds of the present invention are adenosine monophosphate deaminase inhibitors of the following formula (1).

wherein

Y is —C(K)— or nitrogen;

K is hydrogen, halogen, azido, or amino;

G is hydrogen, lower alkyl, or amino;

Z is azido, hydroxy, thio, lower acyloxy, or lower thioacyloxy;

Z' is hydrogen or lower alkyl;

J is hydrogen or lower alkyl;

B is a straight or branched divalent group selected from lower alkylene, lower alkylenylaryl, lower alkylenylamino, lower alkylenylaminoalkylene, lower alkylenylaminoaryl, lower alkylenyloxyaryl, lower alkylenylacylamino, lower alkylenyloxyalkyenylaryl, lower alkylenylacylaminoalkylene, lower alkyleneoxy, lower alkoxyalkyl, lower alkylenethio, lower alkylthioalkyl, lower alkynyl or lower alkenyl, alkylcarboxamidoalkyl, alkylcarboxamidoalkylaryl, hydroxylated lower alkylene, halogenated lower alkylene, halogenated lower alkylenylaryl, alkylenetetrazolo, alkylene-3H-1,2,3,5-oxythiodiazolo, alkylenethiazolidine-2-,4-diono, alkyleneoxazolidin-2, 4-diono or is a direct link;

A is a divalent group selected from a straight or branched alicyclic group, a straight or branched heteroalicyclic group, aryl group or heteroaryl group, all optionally substituted with substituents independently selected from lower alkyl, lower aryl, lower aryloxy, aralkyl, perhaloalkoxy, aralkoxy, heteroaryl, heteroaryloxy, heteroarylalkyl, heteroaralkoxy, azido, amino, guanidino, halogen, hydroxy, lower alkoxy, lower alkylthio, carboxyalkyl, carboxyl, carboxamido, carboxamidoalkylaryl, carboxamidoaryl, aminocarboxamidoalkyl, cyano, lower perhaloalkyl, or is a direct link;

X is hydrogen, lower alkyl, lower alkoxy, halogen, hydroxy, acyloxy, thio, amino, azido, cyano, carboxyl, carboxyalkyl, carboxyaryl, carboxyaralkyl, tetrazolo, 3H-1,2,3,5-oxythiodiazolo, thiazolidine-2-,4-diono, oxazolidin-2,4-diono, carboxamido, carboxamidoalkyl, carboxamidoaralkyl, carboxamidoaryl, guanidino, —PO₃EE', or C(W)CO₂E (COQ);

E and E' are independently selected from hydrogen, lower alkyl, aryl or aralkyl;

W is hydrogen, lower alkyl, halogenated lower alkyl, carboxyalkyl, carboxyaralkyl, or halogen;

Q is lower alkyl, lower alkoxy, aralkoxy, lower alkylthio, alkylamino, hydroxy, amino, arylamino, aralkylamino or aryloxy;

and pharmaceutically acceptable salts thereof;

with the proviso that (a) when B is a direct link, then A is not substituted tetrahydrofuran or substituted cyclopentylene;

(b) when B is lower alkoxyalkyl and A is a direct link, then x is not hydroxy; and (c) when B is methylene and A is a direct link, then X is not hydrogen and (d) when B is methylene, X is hydrogen then A is not phenyl, (e) A and B cannot both be direct links.

Preferred Compounds of Formula 1

Suitable alkyl include groups having from one to about twenty carbon atoms. Suitable aryl groups include groups having from one to about twenty carbon atoms. Suitable aralkyl groups include having from two to about twenty-one carbon atoms. Suitable acyloxy and thioacyloxy groups include groups having from two to about twenty carbon atoms. Suitable alkylene groups include groups having from one to about twenty carbon atoms. Suitable alicylic groups include groups having three to about twenty carbon atoms. Suitable heteroalicyclic groups include groups having from two to about twenty carbon atoms and from one to five heteroatoms, preferably independently selected from nitrogen, oxygen, phosphorous and sulfur.

Preferred are compounds of formula 1 wherein:

B is a divalent straight or branched lower alkylene, straight or branched lower alkylenylaryl, or a direct link;

A is a divalent group selected from a straight or branched alicyclic group; a straight or branched heteroalicyclic group; aryl; or heteroaryl; all optionally substituted with substituents independently selected from amino, halogen, hydroxy, cyano, lower alkyl, lower perhaloalkyl, lower alkoxy, lower aryl, lower aryloxy, aralkyl, aralkoxy, and heteroaryl;

or is a direct link; and X is hydrogen, carboxyl, carboxyalkyl, carboxyaryl, carboxyaralkyl, tetrazolo, 3H-1,2,3,5-oxythiodiazolo, thiazolidine-2-,4-diono, oxazolidin-2,4-diono, or C(W)CO₂E(COQ);

where E and E' are independently selected from hydrogen, lower alkyl, aryl or aralkyl;

W is hydrogen or lower alkyl;

Q is lower alkoxy, aralkylamino, alkylamino, hydroxy, amino, arylamino or aryloxy.

More preferred are compounds wherein:

(a) X is hydrogen and A is a direct link;

(b) X is hydrogen and A is aryl;

(c) X is hydrogen and A is alicyclic;

(d) A is a direct link and x is carboxyl, carboxyalkyl, carboxyaryl, carboxyaralkyl, tetrazolo, 3H-1,2,3,5-oxythiodiazolo, thiazolidine-2-,4-diono, oxazolidin-2, 4-diono;

(e) A is a direct link, and X is C(W)CO₂E(COQ) where E and E' are independently selected from hydrogen, lower alkyl, aryl or aralkyl; W is hydrogen or lower alkyl; and Q is lower alkoxy, aralkylamino, alkylamino, hydroxy, amino, arylamino, aralkylamino or aryloxy; or (f) A is not a direct link and X is carboxyl, carboxyalkyl, carboxyaryl, carboxyaralkyl, tetrazolo, 3H-1,2, 3,5-oxythiodiazolo, thiazolidine-2-,4-diono, oxazolidin-2, 4-diono.

Preferred are compounds where Y is —C(—K)—. Preferred K groups include hydrogen.

Preferred are compounds where G is hydrogen or methyl.

Preferred are compounds where Z is hydroxy or azido and Z' is hydrogen.

Preferred are compounds where Z is hydroxy and Z' is lower alkyl of one to three carbons.

Preferred are compounds where J is hydrogen.

Preferred are compounds where B is straight or branched lower alkylene, lower alkylenylaryl or a direct link.

Preferred are compounds where A is a divalent group selected from a straight or branched alicyclic group, a straight or branched heteroalicyclic group, aryl or heteroaryl, all optionally substituted with substituents independently selected from amino, halogen, hydroxy, cyano, lower alkyl, lower alkoxy, lower aryl, lower aryloxy, aralkyl, perhaloakloxy, aralkoxy, heteroaryl, heteroaryloxy, heteroarylalkyl, heteroaralkoxy or is a direct link.

Preferred are compounds where X is hydrogen, carboxyl, carboxyalkyl, carboxyaryl, carboxyaralkyl, tetrazolo, 3H-1, 2,3,5-oxythiodiazolo, thiazolidine-2-,4-diono, oxazolidin-2, 4-diono, or C(W)CO$_2$g(COQ); where g and E' are independently selected from hydrogen, lower alkyl, aryl or aralkyl; W is hydrogen or lower alkyl; Q is lower alkoxy, aralkoxy, aralkylamino, alkylamino, hydroxy, amino, arylamino or aryloxy.

A preferred group of compounds include compounds where Y is —C(—K)— and K is hydrogen; Z is hydroxy or azido and Z' is hydrogen and the carbon to which they are attached is of the R configuration.

Another preferred group of compounds include compounds where Y is —C(—K)— and K is hydrogen; Z is hydroxy or azido; G and Z' are independently hydrogen or methyl; and J is hydrogen.

More preferred are compounds where Y is —C(—K)— and K is hydrogen; Z is hydroxy or azido; G and Z' are independently hydrogen or methyl; J is hydrogen; B is straight or branched lower alkylene, straight or branched lower alkylenylaryl, or a direct link.

Another more preferred group of compounds comprises those compounds where Y is —C(—K)— and K is hydrogen; Z is hydroxy or azido; G and Z' are independently hydrogen or methyl; J is hydrogen; A is a divalent group selected from a straight or branched alicyclic group, a straight or branched heteroalicyclic group, aryl, or heteroaryl, all optionally substituted with substituents independently selected from amino, halogen, hydroxy, cyano, lower alkyl, lower perhaloalkyl, lower alkoxy, lower aryl, lower aryloxy, aralkyl, aralkoxy, and heteroaryl; or A is a direct link.

An additional group of more preferred compounds are compounds where Y is —C(—K)— and K is hydrogen; Z is hydroxy or azido, G and Z' are independently hydrogen or methyl; J is hydrogen; X is hydrogen, carboxyl, carboxyalkyl, carboxyaryl, carboxyaralkyl, tetrazolo, 3H-1, 2,3,5-oxythiodiazolo, thiazolidine-2-,4-diono, oxazolidin-2, 4-diono, or C(W)CO$_2$E(COQ); where E and E' are independently selected from hydrogen, lower alkyl, aryl or aralkyl; W is hydrogen or lower alkyl; Q is lower alkoxy, aralkoxy, aralkylamino, alkylamino, hydroxy, amino, arylamino or aryloxy.

A further group of more preferred compounds are compounds where Y is —C(—K)— and K is hydrogen; Z is hydroxy or azido, G and Z' are independently hydrogen or methyl; J is hydrogen; B is straight or branched lower alkylene, straight or branched lower alkylenylaryl, or a direct link; A is a divalent group selected from a straight or branched alicyclic group, a straight or branched heteroalicyclic group, aryl, or heteroaryl, all optionally substituted with substituents independently selected from amino, halogen, hydroxy, cyano, lower alkyl, lower perhaloalkyl, lower alkoxy, lower aryl, lower aryloxy, aralkyl, aralkoxy, and heteroaryl; or A is a direct link; X is hydrogen, carboxyl, carboxyalkyl, carboxyaryl, carboxyaralkyl, tetrazolo, 3H-1, 2,3,5-oxythiodiazolo, thiazolidine-2-,4-diono, oxazolidin-2, 4-diono, or C(W)CO$_2$E(COQ); where E and E' are independently selected from hydrogen, lower alkyl, aryl or aralkyl; W is hydrogen or lower alkyl; Q is lower alkoxy, aralkoxy, aralkylamino, alkylamino, hydroxy, amino, arylamino or aryloxy. Especially preferred are those compounds wherein (a) X is hydrogen and A is a direct link; (b) X is hydrogen and A is aryl; (c) X is hydrogen and A is alicyclic; (d) A is a direct link and X is carboxyl, carboxyalkyl, carboxyaryl, carboxyaralkyl, tetrazolo, 3H-1,2,3,5-oxythiodiazolo, thiazolidine-2-,4-diono, oxazolidin-2,4-diono; (e) A is a direct link, and X is C(W)CO$_2$E(COQ) where E and E' are independently selected from hydrogen, lower alkyl, aryl or aralkyl; W is hydrogen or lower alkyl; Q is lower alkoxy, aralkoxy, alkylamino, hydroxy, amino, arylamino, aralkylamino or aryloxy; (f) A is not a direct link and X is carboxyl, carboxyalkyl, carboxyaryl, carboxyaralkyl, tetrazolo, 3H-1, 2,3,5-oxythiodiazolo, thiazolidine-2-,4-diono, oxazolidin-2, 4-diono; (g) B is methylene, A is 1,2-[6,6-dimethyl[3.1.1] bicyclohept-2-methylene] and X is hydrogen; (h) A is cycloheptylene, B is a direct link and X is hydrogen; (i) B is —(CH$_2$)$_4$—, A is a direct link, X is —C(W)CO$_2$E(COQ) where W is hydrogen or methyl, E is aralkyl and Q is hydroxy; (j) B is —(CH$_2$)$_4$-, A is a direct link, X is —C(W)CO$_2$E(COQ) where W is hydrogen or methyl, m is hydroxy, and Q is aralkylamino; (k) B is 1,7-[3,7-dimethyloct-6-enylene], A is a direct link and X is hydrogen; (l) B is —(CH$_2$)2-, and A is 1,3-arylene and X is carboxyl; (m) B is —(CH$_2$)$_2$- and A is optionally substituted naphthalene; (n) B is —(CH$_2$)2-, A is 1,3-(2-methyl)phenylene and X is carboxyl; (o) B is —(CH$_2$)2-, A is 1,3-naphthylene and x is carboxyl; (p) B is —(CH$_2$)2-, A is 1,3-(5-bromo) phenylene and X is carboxyl; (q) B is —(CH$_2$)2-, A is 2,4-thienyl and X is carboxyl; (r) B is 1,5-(6-arylhexylene) and X is carboxyl; (s) B is 1,5-(6-phenylhexylene) and X is carboxyl; (t) B is 1,5-(6-(3-bromophenyl)hexylene) and X is carboxyl; (u) B is alkyl of four to ten carbons, A is a direct link and X is hydrogen; (v) B is heptyl, A is a direct link and X is hydrogen; or (w) B is lower alkylene of two to seven carbons, more preferably two to five and A is aryl, more preferably phenylene, particularly preferred are those compounds where A is 1,2-phenylene and X is methyl or where A is 1,4-phenylene and x is propoxy.

In the following examples of preferred compounds, carboxylic acids are carboxylic acids and derivatives thereof including lower alkyl and lower alkylaryl esters and the known carboxylic acid mimics: tetrazole, 3H-1,2,3,5-oxathiadiazole, thiazolidine-2,4-dione and oxazolidine-2,4-dione.

Examples of preferred compounds include, but are not limited to:

Preferred are the following compounds:

3-(trans-3',7'-dimethyl-2',6'-octadienyl)coformycin aglycone, (3'R)-3-(3',7'-dimethyloct-6'-enyl)coformycin aglycone, 3-cycloheptylcoformycin aglycone (compound 1d), 3-cyclohexylmethylcoformycin aglycone, 3-cycloheptylmethylcoformycin aglycone, (1'S,2'S,5'S)-3-(6',6'-dimethyl[3,1,1]-bicyclohept-2'-methyl) coformycin aglycone (compound 1e), (1'R,2"S,5"R)-3-(2'-(2"-isopropyl-5"-methylcyclohexyloxy) ethyl)coformycin aglycone, 3-(naphth-2'-ylmethyl)coformycin aglycone, 3-(2'-(naphth-1"-yl)ethyl)coformycin aglycone, 3-(2'-(naphth-2"-yl)ethyl)coformycin aglycone, 3-(2'-phenylethyl)coformycin aglycone, 3-(2'-(2"-methylphenyl)ethyl)coformycin aglycone, 3-(6'-carboxyhexyl)coformycin aglycone,
3-(7'-carboxyheptyl)coformycin aglycone,
3-carboxyethylthioethylcoformycin aglycone,
N-(3-(3',6'7',8'-tetrahydroimidazo[4',5'-d]-[1',3']diazepin-8'-ol-3'-yl)propyl)-N-formyl-D-phenylalanine,
N-(3-(3',6'7',8'-tetrahydroimidazo[4',5'-d]-[1',3']diazepin-8'-ol-3'-yl propyl)-N-formyl-L-phenylalanine,
N-(4-(3',6'7',8'-tetrahydroimidazo[4',5'-d]-[1',3']diazepin-8'-ol-3'-yl butyryl)-L-phenylalanine,
2-amino-3-(5'-carboxy-5'-carbobenzyloxypentyl) coformycin aglycone,
2-bromo-3-(5'-carboxy-5'-carbobenzyloxypentyl) coformycin aglycone,
3-(5'-carbox-N-benzylamido-5'-carboxypentyl)-5-methylcoformycin aglycone,
3-(5'-carbox-N-benzylamido-5'-carboxypentyl)-8-methylcoformycin aglycone,
3-(5'-carbox-N-(4"-chlorobenzyl)amido-5'-carboxypentyl) coformycin aglycone,
3-(5'-carboxamido-5'-carboxyhexyl)coformycin aglycone,
3-(2'-(o-carboxyphenylthio)ethyl)coformycin aglycone,
3-(3'-(3"-carboxy-6"-methylphenyl)propyl)coformycin aglycone,
3-(3'-(2"-methoxy-5"-carboxyphenyl)propyl)coformycin aglycone,
3-(3"-carboxy-6"-propylphenyl)ethyl)coformycin aglycone,
3-(3"-carboxy-6"-hydroxymethylphenyl)ethyl)coformycin aglycone,
3-(2'-(3"-carboxyphenyl)ethyl)coformycin aglycone,
3-(3'-(2"-carboxy-3"-fluorophenyl)propyl)coformycin aglycone,
3-(3'-(2"-carboxythiophen-3"-yl)propyl)coformycin aglycone,
3-(2'-(2"-carboxythiophen-5"-yl)ethyl)coformycin aglycone,
3-(3'-(2"-carboxynaphthyl)propyl)coformycin aglycone,
2-bromo-3-(2'-3"-carboxynaphthyl)ethyl)coformycin aglycone,
2-amino-3-(2'-carboxynaphthyl)ethyl)coformycin aglycone,
2-amino-3-(2'-(3"-bromo-5"-carboxyphenyl)ethyl) coformycin aglycone,
2-bromo-3-(2'-3"-bromo-5"-carboxyphenyl)ethyl) coformycin aglycone,
2-bromo-3-(5'-carboxy-6'-(3"-bromophenyl)hexyl) coformycin aglycone,
2-amino-3-(5'-carboxy-6'-(3"-bromophenyl)hexyl) coformycin aglycone,
3-[2'-(7"-carboxybenzopyran-5"-yl)ethyl]coformycin aglycone,
3-[2'-(6"-carboxybenzopyran-8"-yl)ethyl]coformycin aglycone,
3-[2'-(3"-carboxy-5",6",7",8"-tetrahydronaphthyl) ethyl] coformycin aglycone,
3-[2'-(3"-carboxy-5",7"-benzodioxolyl)ethyl]coformycin aglycone,
3-[2'-(6"-carboxy-2",3"-dihydrobenzofuran-4"-yl )ethyl]-coformycin aglycone,
3-[2'-3"-carboxyindane)ethyl]coformycin aglycone,
3-[2'-5"-carboxy-2",3"-dihydrobenzofuran-7"-yl )ethyl]-coformycin aglycone,
3-[2'-(6"-carboxybenzothiophen-4"-yl)ethyl]coformycin aglycone,
3-[2'-(6"-carboxybenzofuran-4"-yl)ethyl]coformycin aglycone,
3-[2-(3"-carboxyanthracenyl)ethyl]coformycin aglycone,
3-[2'-(3"-carboxacenaphthylenyl)ethyl]coformycin aglycone,
3-[2'-(3"-carboxyphenanthrenyl)ethyl]coformycin aglycone,
3-(6'-carboxy-6'-carbobenzyloxyhexyl)coformycin aglycone,
3-(5'-carboxy-6'-carbobenzyloxyhexyl)coformycin aglycone,
3-(5'-carboxy-5',5'-dibenzylpentyl)coformycin aglycone,
3-(5'-carboxy-5'-fluoro-6'-phenylhexyl)coformycin aglycone,
3-(5'-carboxy-6'-(2"-chlorophenyl)hexyl)coformycin aglycone,
3-(5'-carboxy-6'-(2"-iodophenyl)hexyl)coformycin aglycone,
3-(5'-carboxy-6'-(2"-tolyl)hexyl)coformycin aglycone
3-(5'-carboxy-6'-(2"-trifluoromethylphenyl)hexyl) coformycin aglycone,
3-(5'-carboxy-6'-(2"-ethoxyphenyl)hexyl)coformycin aglycone,
3-(5'-carboxy-6'-(2"-benzyloxyphenyl)hexyl)coformycin aglycone,
3-(5'-carboxy-6'-(2"-hydroxyphenyl)hexyl)coformycin aglycone,
3-(5'-carboxy-6'-(4"-fluorophenyl)hexyl)coformycin aglycone,
3-(5'-carboxy-5'-(4"-fluorophenoxypentyl)coformycin aglycone,
3-(5'-carboxy-5'-hydroxy-6'-phenylhexyl)coformycin aglycone,
3-(5'-carboxy-5'-phenoxypentyl)coformycin aglycone,
3-(5'-carboxy-5'-(4"-chlorophenoxypentyl)coformycin aglycone,
3-(5'-carboxy-5'-benzyloxypentyl)coformycin aglycone,
3-(5'-carboxy-5'-(4"-chlorobenzyloxy)pentyl)coformycin aglycone,
3-(5'-carboxy-5'-(3"-bromophenoxypentyl)coformycin aglycone,
3-(3'-(2"-bromo-4"-propoxyphenyl)propyl)coformycin aglycone,
3-(3'-(2"-chloro-4"-propoxyphenyl)propyl)coformycin aglycone,
3-[2'-(3"-Carboxy-6",8"-dichloronaphthyl)ethyl] coformycin aglycone,
3-[2'-(3-Carboxy-6", 8"-difluoronaphthyl)ethyl]coformycin aglycone,
3-[2'-(3"-Carboxy-6", 8"-ditrifluoromethylnaphthyl) ethyl] coformycin aglycone,
3-[2'-(3"-Carboxy-8"-chloronaphthyl)ethyl]coformycin aglycone,
3-[2'-(3"-Carboxy-8"-trifluoromethylnaphthyl)ethyl] coformycin aglycone,
3-[2'-(3"-Carboxy-8"-methylnaphthyl)ethyl]coformycin aglycone,
3-[2'-(3"-Carboxy-8"-fluoronaphthyl)ethyl]coformycin aglycone,
3-[2'-(3"-Carboxy-7"-chloronaphthyl)ethyl]coformycin aglycone,
3-[2'-(3"-Carboxy-7"-bromonaphthyl)ethyl]coformycin aglycone,
3-[2'-(3"-Carboxy-7"-trifluoromethylnaphthyl)ethyl] coformycin aglycone,
3-[2'-(3"-Carboxy-7"-methylnaphthyl)ethyl ]coformycin aglycone,
3-[2'-(3"-Carboxy-7"-fluoronaphthyl)ethyl ]coformycin aglycone,
3-[2'-(3"-Carboxy-7"-phenoxynaphthyl)ethyl]coformycin aglycone,
3-[2'-(3"-Carboxy-7"-phenylnaphthyl)ethyl]coformycin aglycone, 3-[2'-(3"-Carboxy-7"-ethylnaphthyl)ethyl]coformycin aglycone,
3-[2'-(3"-Carboxy-5"-(p-chlorophenoxy)naphthyl)ethyl] coformycin aglycone,
3-[2'-(3"-Carboxy-5"-phenoxynaphthyl)ethyl]coformycin aglycone,
3-[2'-(3-Carboxy-5",6",7"-trifluoronaphthyl)ethyl] coformycin aglycone,
3-[2'-(3"-Carboxy-5",6"-difluoronaphthyl)ethyl]coformycin aglycone,
3-[2'-(3"-Carboxy-5",7"-difluoronaphthyl)ethyl]coformycin aglycone,
3-[2'-(3"-Carboxy-6"-bromo-7"-fluoromethylnaphthyl) ethyl]coformycin aglycone,
3-[2'-(3"-Carboxy-9"-methoxyphenanthrene)ethyl] coformycin aglycone and
3-[2'-(2"-Carboxy-4"-phenanthrene)ethyl]coformycin aglycone.

More preferred are the following compounds:
3-heptylcoformycin aglycone (compound 1a),
3-heptyl-8-methylcoformycin aglycone (compound 1b),
3(4'-benzylcycloheptyl)coformycin aglycone,
3-(4'-(2"-phenylethyl)cycloheptyl)coformycin aglycone,
3-(3'-benzylcycloheptyl)coformycin aglycone,
3-(3'-(2"-phenylethyl)cycloheptyl)coformycin aglycone,
3-(3'-cyclohexylpropyl)coformycin aglycone,
3-2'-(2"-ethoxynaphth-1"-yl)ethyl)coformycin aglycone,
3-2'-(3"-ethoxynaphth-1"-yl)ethyl)coformycin aglycone,
3-(2'-(4"-ethoxynaphth-1"-yl)ethyl)coformycin aglycone,
3-(2'-(5"-ethoxynaphth-1"-yl)ethyl)coformycin aglycone,
3-(2'-(6"-ethoxynaphth-1"-yl)ethyl)coformycin aglycone,
3-(2'-(7"-ethoxynaphth-1"-yl)ethyl)coformycin aglycone,
3-(2'-(8"-ethoxynaphth-1"-yl)ethyl)coformycin aglycone,
3-(2'-(naphth-2"-yl)ethyl)coformycin aglycone,
3-(2'-(1"-ethoxynaphth-2"-yl)ethyl)coformycin aglycone,
3-(2'-(3"-ethoxynaphth-2"-yl)ethyl)coformycin aglycone,
3-(2'-(4"-ethoxynaphth-2"-yl)ethyl)coformycin aglycone,
3-(2'-(5"-ethoxynaphth-2"-yl)ethyl)coformycin aglycone,
3-(2'-(6"-ethoxynaphth-2"-yl)ethyl)coformycin aglycone,
3-(2'-(7"-ethoxynaphth-2"-yl)ethyl)coformycin aglycone,
3-(2'-(8"-ethoxynaphth-2"-yl ethyl)coformycin aglycone,
3-(2'-(2"-propoxynaphth-1"-yl)ethyl)coformycin aglycone,
3-(2'-(3"-propoxynaphth-1"-yl)ethyl)coformycin aglycone,
3-(2'-(4"-propoxynaphth-1"-yl)ethyl)coformycin aglycone,
3-(2'-(5"-propoxynaphth-1"-yl)ethyl)coformycin aglycone,
3-(2'-(6"-propoxynaphth-1"-yl)ethyl)coformycin aglycone,
3-(2'-(7"-propoxynaphth-1"-yl)ethyl)coformycin aglycone,
3-(2'-8"-propoxynaphth-1"-yl ethyl)coformycin aglycone
3-(2'-1"-propoxynaphth-2"-yl ethyl)coformycin aglycone
3-(2'-3"-propoxynaphth-2"-yl ethyl)coformycin aglycone
3-(2'-4"-propoxynaphth-2"-yl ethyl)coformycin aglycone
3-(2'-5"-propoxynaphth-2"-yl ethyl)coformycin aglycone
3-(2'-6"-propoxynaphth-2"-yl ethyl)coformycin aglycone
3-(2'-7"-propoxynaphth-2"-yl ethyl)coformycin aglycone
3-(2'-8"-propoxynaphth-2"-yl ethyl)coformycin aglycone
3-(3'-phenylpropyl)coformycin aglycone,
3-(3'-(2"-methylphenyl)propyl)coformycin aglycone (compound 1f),
5-methyl-3-(3'-(2"-methylphenyl)propyl)coformycin aglycone (compound 1g),
3-(3'-propylphenyl)-8-azido-3,6,7,8-tetrahydroimidazo[4,5-d][1,3]diazepine (compound 1h),
3-(3'-(2"-trifluoromethylphenyl)propyl)coformycin aglycone,
3-(3'-(3"-methylthiophen-2"-yl)propyl)coformycin aglycone,
3-(3'-2"-chlorophenyl)propyl)coformycin aglycone,
3-(3'-3"-chlorophenyl)propyl)coformycin aglycone,
3-(3'-2"-bromophenyl)propyl)coformycin aglycone,
3-(3'-3"-bromophenyl)propyl)coformycin aglycone,
3-(3'-2"-ethoxyphenyl)propyl)coformycin aglycone,
3-(3'-3"-ethoxyphenyl)propyl)coformycin aglycone,
3-(3'-4"-ethoxyphenyl)propyl)coformycin aglycone,
3-(3'-2"-benzyloxyphenyl)propyl)coformycin aglycone,
3-(3'-(3"-benzyloxyphenyl)propyl)coformycin aglycone,
3-(3'-(4"-trifluoromethoxyphenyl)propyl)coformycin aglycone,
3-(3'-(4"-butoxyphenyl)propyl)coformycin aglycone,
3-(3'-(4"-isopropylphenyl)propyl)coformycin aglycone,
3-(3'-(4"-propylphenyl)propyl)coformycin aglycone,
3-(3'-(biphenyl-4"-yl)propyl)coformycin aglycone,
3-(3'-(2",4"-dimethylphenyl)propyl)coformycin aglycone,
3-(3'-(2",4",6"-trimethylphenyl)propyl)coformycin aglycone,
3-(3'-(2"-hydroxyphenyl)propyl)coformycin aglycone,
3-(3'-(4"-hydroxyphenyl)propyl)coformycin aglycone,
3-(5'-carboxypentyl)coformycin aglycone,
3-(5'-(tetrazol-5"-yl)pentyl)coformycin aglycone,
3-(5'-carbobenzyloxy-5'-carboxyhexyl)coformycin aglycone,
3-(5'-carboxy-6'-phenylhexyl)coformycin aglycone (compound 1j),
3-(5'-carboxy-6'-(2"-bromophenyl)hexyl)coformycin aglycone,
3-(5'-carboxy-6'-(4"-bromophenyl)hexyl)coformycin aglycone,
3-(5'-carboxy-5'-carbobenzyloxypentyl)-5-methylcoformycin aglycone,
3-(5'-carboxy-5'-carbobenzyloxypentyl)-8-methylcoformycin aglycone,
3-(5'-carbox-N-benzylamido-5'-carboxypentyl)coformycin aglycone,
3-(5'-carbox-N-(3"-bromobenzyl)amido-5'-carboxypentyl) coformycin aglycone,
3-(5'-carbox-N-(3"-bromobenzyl)amido-5'-carboxypentyl)-5-methylcoformycin aglycone,
3-(5'-carbox-N-(3"-bromobenzyl)amido-5'-carboxypentyl)-8-methylcoformycin aglycone,
3-(5'-carbox-N-cyclohexylmethylamido-5'-carboxypentyl) coformycin aglycone,
3-(5'-carbox-N-benzylamido-5'-carboxyhexyl)coformycin aglycone (compound 1l),
3-(5'-carbox-N-(2"-phenethyl)amido-5'-carboxyhexyl) coformycin aglycone,
3-(5'-carbox-N-cyclohexylamido-5'-carboxyhexyl) coformycin aglycone,
3-(5'-carbox-N-Cyclohexylmethylamido-5'-carboxyhexyl) coformycin aglycone,
3-(3'-(2"-fluoro-5"-carboxyphenyl)ethyl)coformycin aglycone,
3-(2'-(2"-methoxy-5"-carboxyphenyl)ethyl)coformycin aglycone,
3-(2'-(3"-carboxy-4"-methylphenyl)ethyl)coformycin aglycone,
3-(2'-(3"-carboxy-4"-fluorophenyl)ethyl)coformycin aglycone,
3-(2'-(3"-carboxy-5"-ethylphenyl)ethyl)coformycin aglycone,
3-(2'-(3"-carboxybiphen-5"-yl)ethyl)coformycin aglycone,
3-(2'-(3"-carboxy-6"-methylphenyl)ethyl)coformycin aglycone (compound 1m),
3-(2'-(6"-methyl-3"-(tetrazol-5'"-yl)phenyl)ethyl) coformycin aglycone (compound 1n),
3-(2'-(3"-carboxy-6"-ethylphenyl)ethyl)coformycin aglycone, 3-(2'-(2"-carboxythiophen-4"-yl ethyl)coformycin aglycone (compound 1o),
3-(3"-carboxynaphthyl)ethyl -5-methylcoformycin aglycone,
3-(2'-(3"-carboxynaphthyl)ethyl-8-methylcoformycin aglycone,
3-(2'-(3"-bromo-5"-carboxyphenyl)ethyl)-5-methylcoformycin aglycone,
3-(2'-(3-bromo-5--carboxyphenyl)ethyl)-8-methylcoformycin aglycone,
3-(5'-carboxy-6'-(3"-bromophenyl)hexyl)-5-methylcoformycin aglycone,
3-(5'-carboxy-6'-(3"-bromophenyl)hexyl)-8-methylcoformycin aglycone,
3-[2'-(2"-chloro-5"-carboxyphenyl)ethyl]coformycin aglycone,
3-[2'-(2",3"-dichloro-5"-carboxyphenyl)ethyl]coformycin aglycone,
3-[2'-(2"-trifluoromethyl-5"-carboxyphenyl)ethyl] coformycin aglycone,
3-[2'-(3"-carboxy-5"-pentafluoroethylphenyl)ethyl] coformycin aglycone,
3-[2'-(3"-carboxy-6"-pentafluoroethylphenyl)ethyl] coformycin aglycone,
3-[2'-(2"-chloro-3"-carboxyphenyl)ethyl]coformycin aglycone,
3-[2'-2"-fluoro-3"-carboxyphenyl)ethyl]coformycin aglycone,
3-[2'-2"-carboxythiophen-4-yl)ethyl]coformycin aglycone,
3-[2'-2"-carboxyfuran-4-yl)ethyl]coformycin aglycone,
3-[2'-3"-carboxy-5"-chloronaphthyl)ethyl]coformycin aglycone,
3-[2'-3"-carboxy-5"-bromonaphthyl)ethyl]coformycin aglycone,
3-[2'-3"-carboxy-5"-trifluoromethyl naphthyl)ethyl] coformycin aglycone,
3-[2'-(3"-carboxy-5"-methylnaphthyl)ethyl]coformycin aglycone,
3-[2'-(3"-carboxy-5"-fluoronaphthyl)ethyl]coformycin aglycone,
3-[2'-(3"-carboxy-6"-chloronaphthyl)ethyl]coformycin aglycone,
3-[2'-(3"-carboxy-6"-bromonaphthyl)ethyl]coformycin aglycone,
3-[2'-(3"-carboxy-6"-trifluoromethyl naphthyl)ethyl] coformycin aglycone,
3-[2'-(3"-carboxy-6"-methylnaphthyl)ethyl]coformycin aglycone,
3-[2'-(3"-carboxy-6"-fluoronaphthyl)ethyl]coformycin aglycone,
3-[2'-(3'-carboxy-2"-chloronaphthyl)ethyl]coformycin aglycone,
3-[2'-(3"-carboxy-2"-fluoronaphthyl)ethyl]coformycin aglycone,
3-(5'-benzyl-5'-carboxy-5'-carbobenzyloxypentyl) coformycin aglycone,
3-(5'-carboxy-5'-carbox-N-benzylamidopentyl)coformycin aglycone,
3-(5'-carboxy-5'-carbox-N-cyclohexylamidopentyl) coformycin aglycone,
3-(5'-carboxy-5'-carbox-N-hexylamidopentyl)coformycin aglycone,
3-(5'-carboxy-5'-carbox-N-(4"-chlorobenzyl)amidopentyl)-coformycin aglycone.
Most preferred are the following compounds:
(3'S)-3-(3',7'-dimethyloct-6'-enyl)coformycin aglycone (compound 1c),
3-(3'-(4"-propoxyphenyl)propyl)coformycin aglycone (compound 1i),
3-(5'-carboxy-5'-carbobenzyloxypentyl coformycin aglycone (compound 1k),
3-(2'-(3"-carboxynaphthyl)ethyl)coformycin aglycone (compound 1p),
3-(2'-(3"-bromo-5"-carboxyphenyl)ethyl coformycin aglycone (compound 1q),
3-(5'-carboxy-6'-(3"-bromophenyl)hexyl)coformycin aglycone (compound 1r).

Synthesis of Preferred Compounds

Preparation of Compounds of Formula 1

The synthesis of compounds of the present invention can be viewed as consisting of the following steps: (1) preparation of the heterocycle, (2) preparation of the electrophile, (3) coupling of the electrophile and the heterocycle, (4) reduction of 8-keto intermediate, if required, and (5) modification of the coupled molecule, if required. Each step is discussed below. The key transformation in this preparation, the coupling step, is shown below, as is the numbering system of the coformycin aglycone.

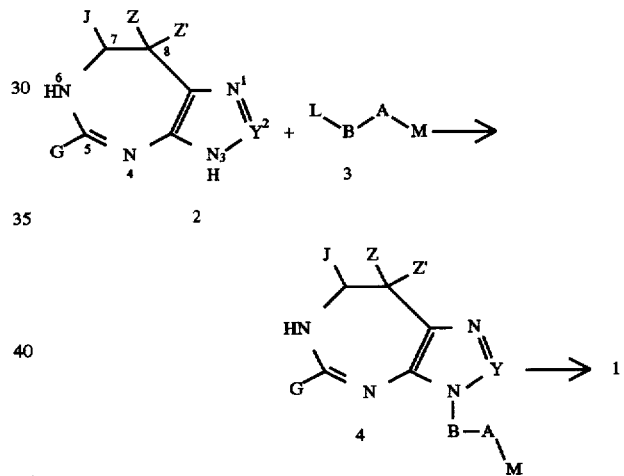

(1) Preparation of the Heterocycle

The heterocycle, compound 2, is preferably prepared by the method of Chan, et al., *J. Org. Chem.* 1982, 47, 3457–3464, with the alteration that the final intermediate is treated with triethylamine in $CH_2Cl_2$ to generate the non-DMSO solvate freebase. The final step of this procedure may employ lower alkyl ortho esters, for example (EtO)$_3CCH_3$, to produce compounds of formula 2 where G is lower alkyl, for example methyl (as shown by Showalter, et al., *J. Med. Chem.* 1983, 26, 1478–1482).

Compounds of formula 2 where Y is nitrogen may be prepared by a modification of the route of Acevedo, et al., *J. Org. Chem.* 1986, 51, 1050–1058. By starting with an appropriate alkyl azide, a precursor to compound 2 may be obtained where R is a suitable protecting group such as benzyl (removable under $Pd(OH)_2$ catalyzed hydrogenation). Alternatively, for compounds where R is B-A-M, this procedure constitutes a synthesis of compounds of formula 4.

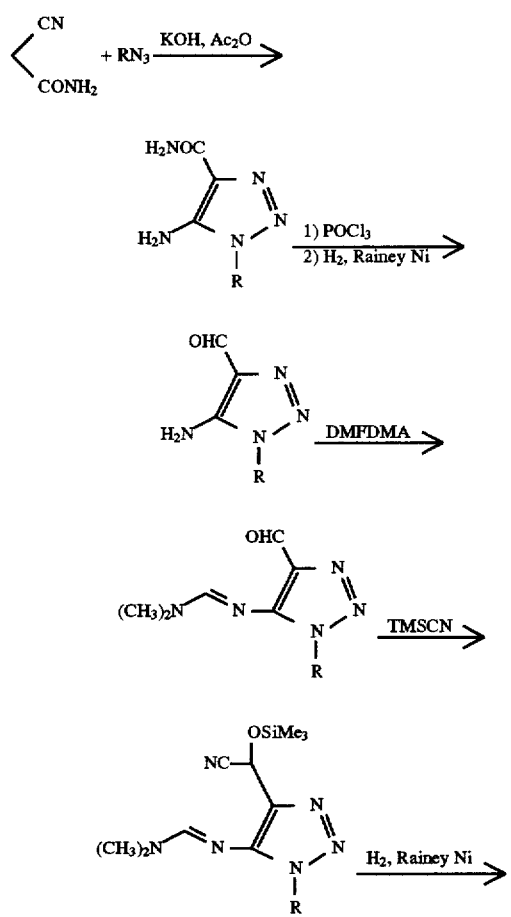

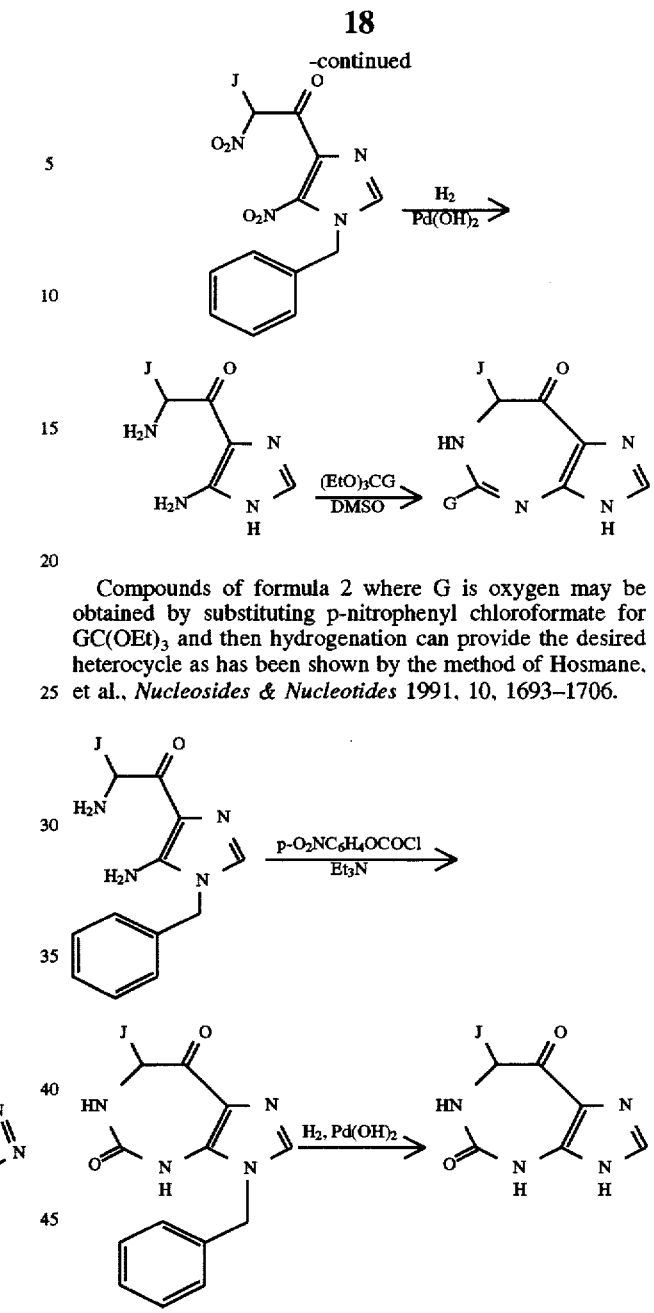

Compounds of formula 2 where G is oxygen may be obtained by substituting p-nitrophenyl chloroformate for GC(OEt)$_3$ and then hydrogenation can provide the desired heterocycle as has been shown by the method of Hosmane, et al., *Nucleosides & Nucleotides* 1991, 10, 1693–1706.

An intermediate step in the method of Chan, et al., *J. Org. Chem.* 1982, 47, 3457–3464 can be modified to employ nitro lower alkanes and the latter steps modified as shown below to provide compounds of formula 2 where J is lower alkyl.

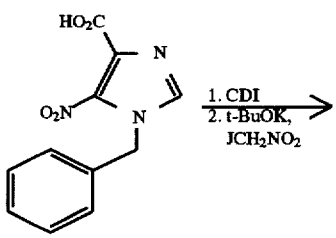

A compound of the formula 2 where the absolute configuration at C8 is R may be obtained by the method of Truong and Rapoport J. Org. Chem. 1993, 58, 6090–6096, starting with L-methionine methyl ester to provide a protected form of 2 shown below.

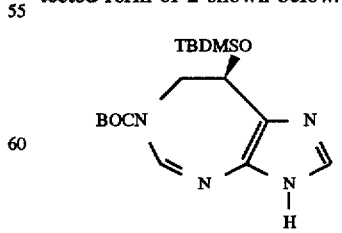

2) Preparation of the Electrophile

One method for the production of electrophile 3, shown below, involves treatment of an active hydrogen compound MH (where M is carboxyimidazole, carboxypyrazole, carboxypyrrole, $HPO_3R_2$, $HC(W)(CO_2R)(COQ)$, optionally substituted phenols or thiophenols, substituted mercaptans and dialkylamines, and where W is alkyl, halogen or carboxyalkyl)with a base, preferably NaH or $K_2CO_3$, in a polar aprotic solvent (such as DMF or DMSO) or with an amine in an alcohol (such as ethanol), and with a precursor electrophile (where L and L' are independently selected leaving groups, preferably both bromine, or L is a leaving group and L' is some group, preferably protected hydroxyl, which can be later modified to a leaving group, such as bromide or mesylate).

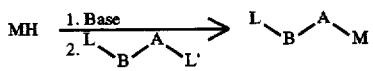

Further, the generalized preparation of precursors of the type MH are illustrated below. Typically, the active hydrogen compound is deprotonated by a suitable base, preferably sodium hydride and the resulting anion alkylated with an appropriate derivative.

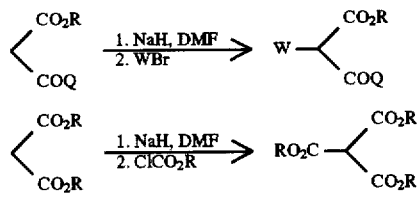

An alternative preparation of electrophile 3, from the corresponding alcohol, is shown below. Treatment, for example, with mesyl chloride and triethylamine in methylene chloride provides the mesylate. If desired, the mesyl group may be exchanged with bromide by treatment with tetrabutylammonium bromide. Alternatively, treatment of the alcohol with $CBr_4$, $PPh_3$ and imidazole provides the bromide directly.

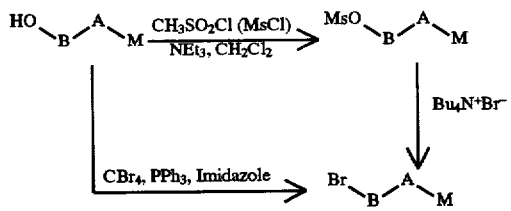

A preparation of the alkoxy or alkylthio part of substituent B in compound 3 is shown below. Coupling of the precursor alcohol with either an additional alcohol or thiol in the presence of triphenylphosphine and diethyl azodicarboxylate (DEAD) gives the desired product.

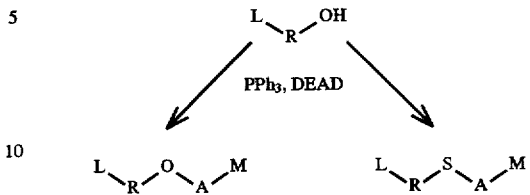

An alternate method, shown below, is to treat the alcohol with paraformaldehyde and HCl to produce the chloromethyl ether.

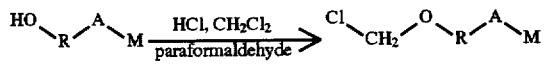

When M in compound 3 is azido, it may be prepared as shown below for the ethyl derivative.

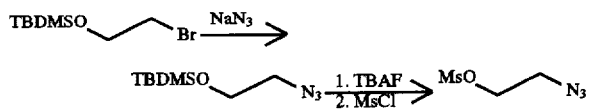

When substituent A in compound 3 is cyclopropane and M is an ester, the compound may be prepared by treatment of an olefin with ethyl diazoacetate in the presence of a catalyst, preferably $Rh_2(OAc)_4$, as shown below.

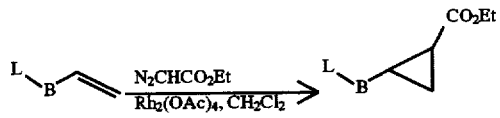

When substituent A in compound 3 is a direct bond and B is a branched alkyl unit with the branching groups R' and R" being optionally H, lower alkyl or arylalkyl, preferably α to a carboxylate group, it may be prepared as outlined below. Stepwise alkylation of an appropriate ester or lactone using a base, such as lithium diisopropylamide, and an appropriate alkyl bromide, followed by a second alkylation gives the desired product.

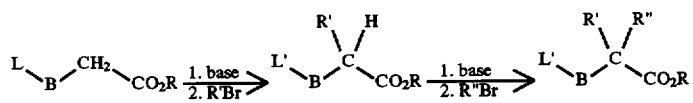

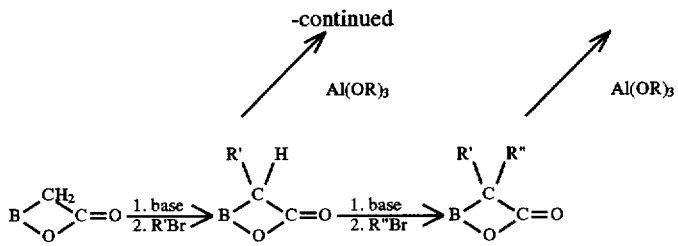

Alternatively, when substituent A in compound 3 is a direct bond and B is a branched alkyl unit with a branching group being optionally aryloxy or hydroxy preferably α to a carboxylate group, it may be prepared as outlined below where in the case of the hydroxy branch the TBDMS ether is converted to the final hydroxy form using TBAF after coupling the electrophile to the heterocycle. The sequence below can also be applied if the branch is a fluorine atom when a fluorine is substituted for the TBDMSoxy group.

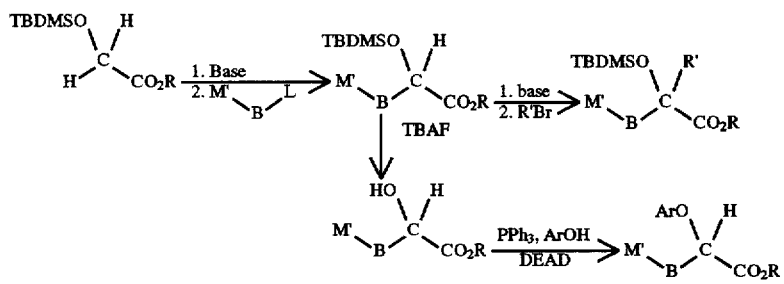

Compound 3 where A is optionally substituted aryl may be prepared as below starting from the appropriate aromatic precursor; where L is a leaving group, preferably iodide, bromide or trifluoromethylsulfonate. Treatment with propargyl alcohol in the presence of diethylamine with palladium catalyst produces a compound which in turn is hydrogenated and then converted to the final bromide or mesylate. The method is applicable to the synthesis of isomers where M is on other positions of the ring and when the ring is optionally heterocyclic. The side chain can be lengthened by substituting terminal alkyne alcohols longer than propargyl alcohol.

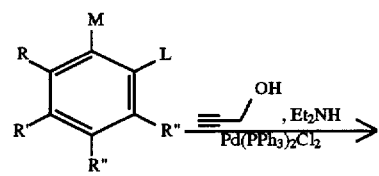

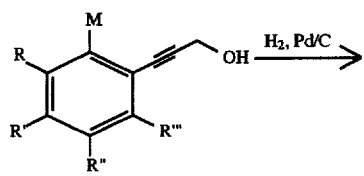

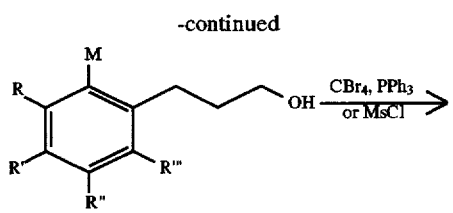

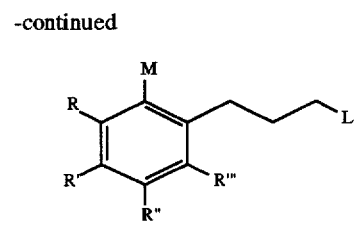

An alternate preparation of propylphenyl electrophiles is shown in the following equation. By subjecting a cinnamic acid to LiAlH$_4$ reduction followed by hydrogenation if necessary and finally mesylation, the desired electrophile may be obtained.

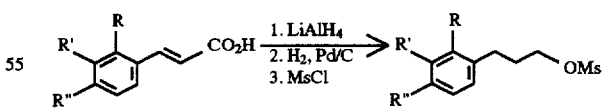

The electrophile in which the alkyl sidechain is shorter by one carbon may be prepared as shown below. Treatment of the starting material with the palladium coupling conditions using allyltributylstannane as the nucleophile produces the adduct which is ozonized and reduced with sodium borohydride to the alcohol which may be converted into the appropriate leaving group.

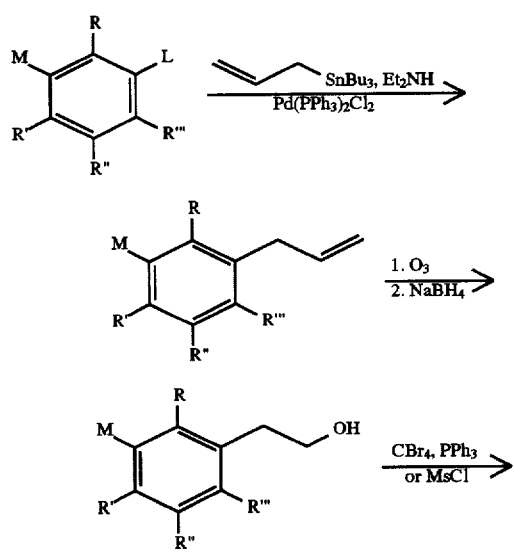

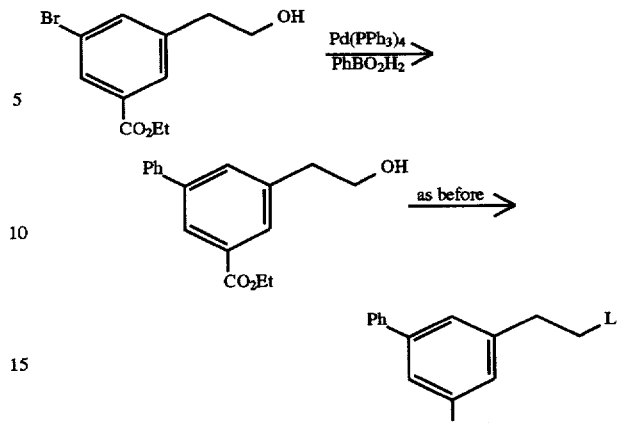

Substituted naphthalenes can be prepared by a known method which is illustrated in the following scheme. Thus, starting from a benzaldehyde, substituted carboxynaphthyl electrophiles may be prepared.

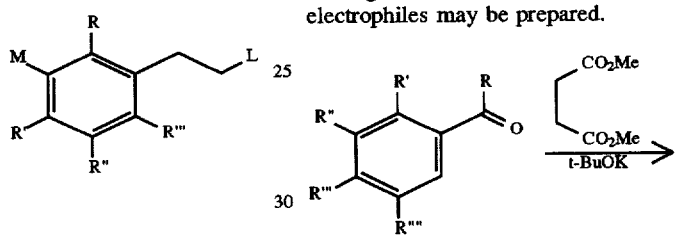

Alternatively, the ethyl sidechain may be incorporated by substituting vinyltributylstannane for allyltributylstannane which provides a vinyl derivative. This after hydroboration and oxidation gives an alcohol which after conversion to a leaving group L provides the desired compound as shown below.

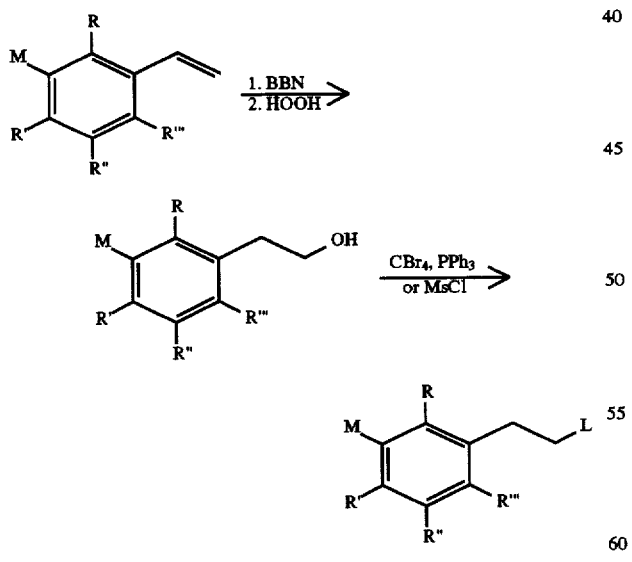

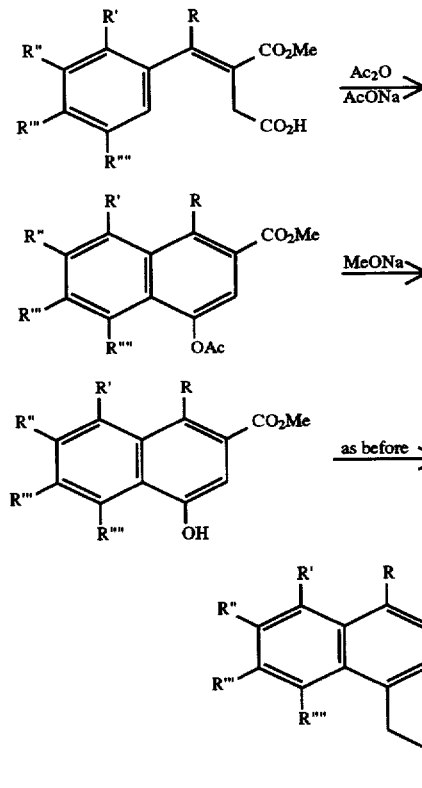

An aryl group Can be substituted with a phenyl ring using phenylboronic acid and palladium catalysis as in the following example with further elaboration providing the desired electrophile.

An alternate preparation of an aryl containing electrophile involves reducing an iodobenzoic acid to the aldehyde, vinylation and then lithiation followed by ethyl chloroformate quench. Elaboration as before would provide the desired electrophile.

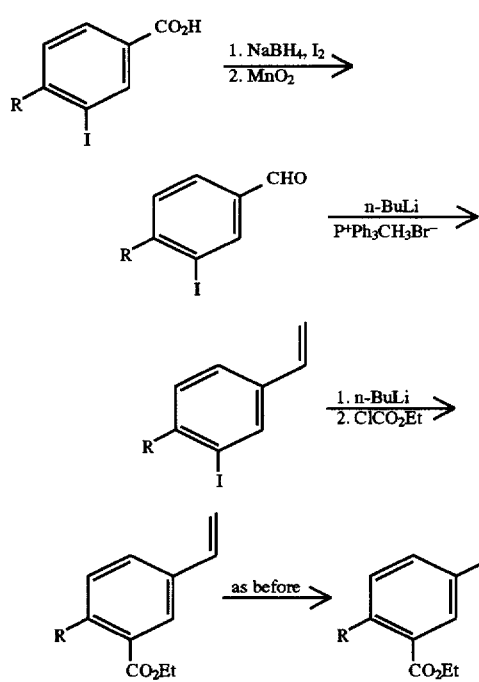

A variation on this scheme is shown below and requires a bromobenzaldehyde to be methoxycarbonylated before elaboration of the formyl group into the bromoethyl sidechain as before.

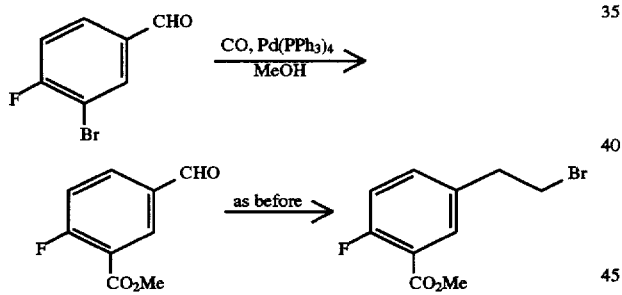

Vinylation of a bromophenylacetate and oxidation of the double bond can provide an aldehyde which is further modified to a bromoalkylphenylacetic acid ester as an electrophile.

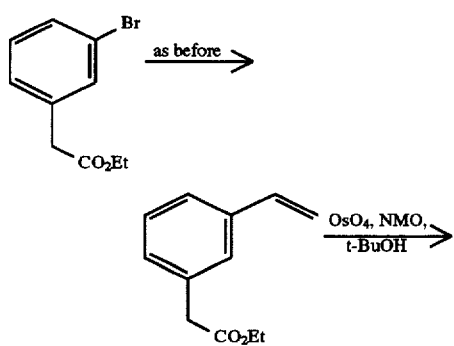

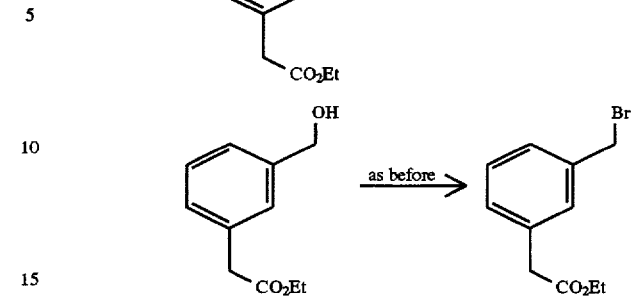

A hydroxymethyl substituted aryl electrophile may be obtained from bromination of a toluate on the methyl group followed by displacement of the bromide with hydroxide and protection of the resulting alcohol as a TBDMS ether. Further elaboration as previously described provides the desired electrophile.

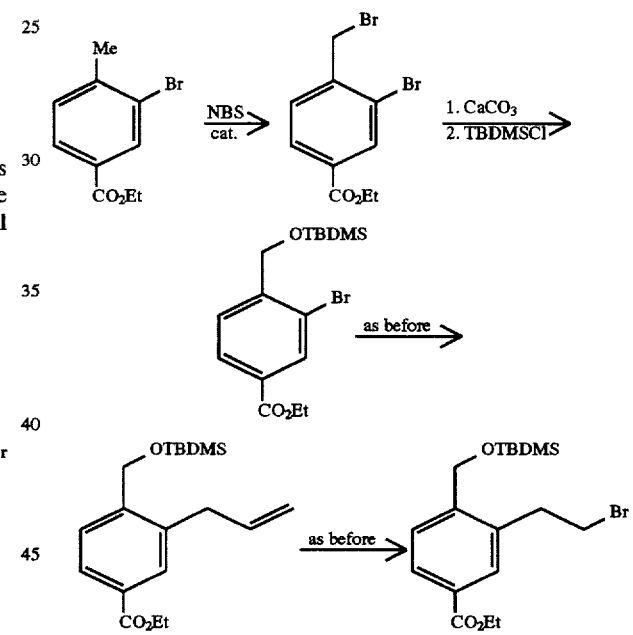

Some other alternately substituted arylester electrophiles may be obtained as shown below. Rearrangement of a phenylallyl ether provides a 2-allyl substituted phenol which after modification as before provides a TBDMS protected hydroxyethyl sidechain. The phenol is converted to a triflate and vinylated or allylated as before. Hydrogenation gives an ethyl or propyl sidechain. TBDMS deprotection and conversion to a bromide by previously described conditions provides the desired electrophiles.

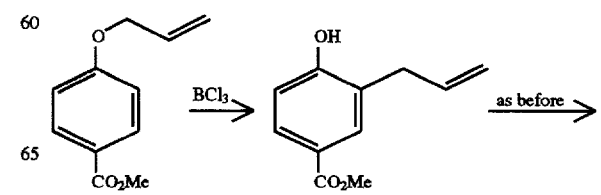

-continued

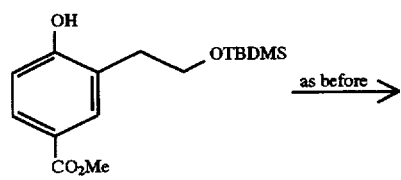

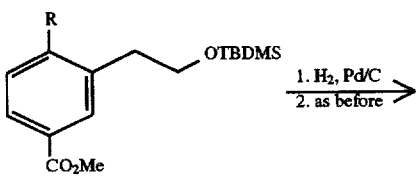

R = vinyl or allyl

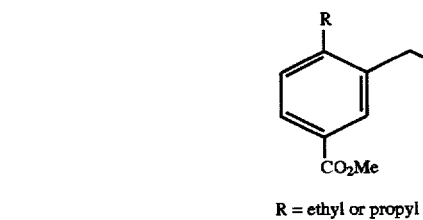

R = ethyl or propyl

Construction of electrophiles where substituent A is a heteroaryl may also be accomplished beginning with substituted furan or thiophene (X' being O or S respectively). The alcohol is protected, preferably as t-butyldimethylsilyl ether, using standard methods and the product is deprotonated with n-butyllithium and then treated with a suitable chloroformate to give the carboalkoxy substituted heterocycle. Desilylation and conversion to the bromide by previously described conditions provides the desired electrophile.

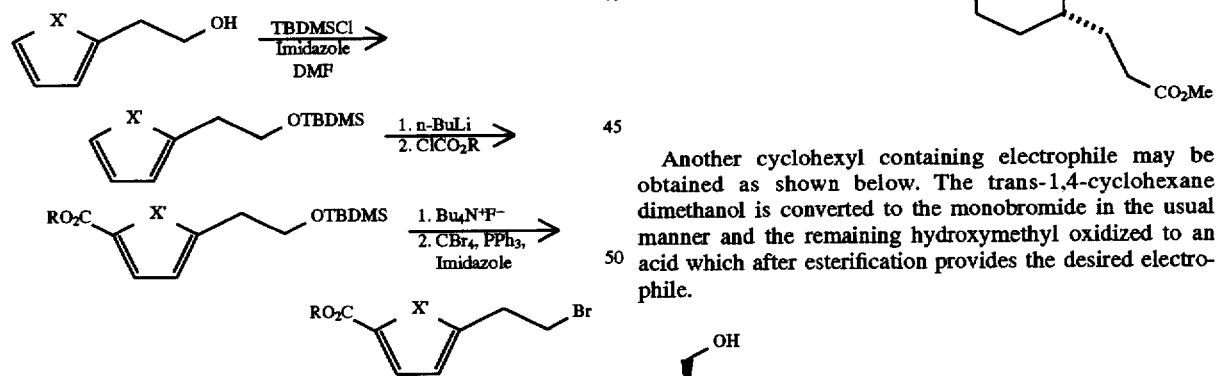

One furanyl starting material (X=O) may be prepared as below. Reaction of 2-furaldehyde with methoxymethyltriphenylphosphonium bromide and n-butyllithium provides a vinyl ether which after hydrolysis and NaBH$_4$ reduction provides the desired alcohol.

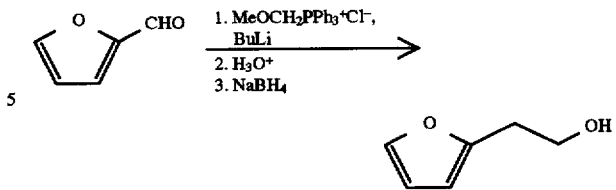

A 1,2-cis-substituted cyclohexyl electrophile may be obtained as shown below. cis-Cyclohexane dimethanol can be oxidized to a lactone which after reduction to a lactol undergoes coupling to form an acrylate. Hydrogenation and conversion to the bromide provides the desired electrophile.

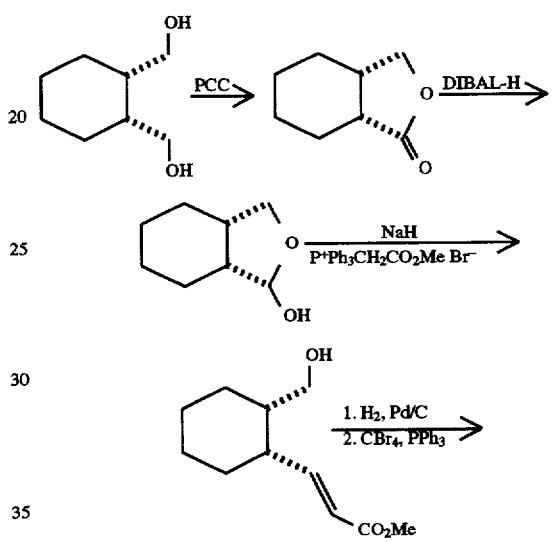

Another cyclohexyl containing electrophile may be obtained as shown below. The trans-1,4-cyclohexane dimethanol is converted to the monobromide in the usual manner and the remaining hydroxymethyl oxidized to an acid which after esterification provides the desired electrophile.

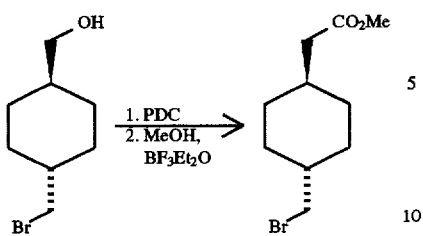
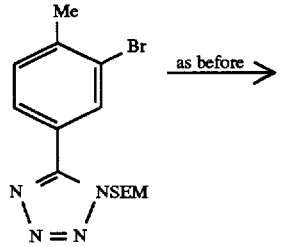

A method to make tetrazole containing electrophiles is shown below. Treatment of tetrazole with a base, preferably NaH, and trimethylsilylethoxymethylchloride (SEM-Cl) forms the protected tetrazole, which may be deprotonated at C5 with t-BuLi in a THF/DMPU solvent system. Addition of the electrophile provides the desired adduct.

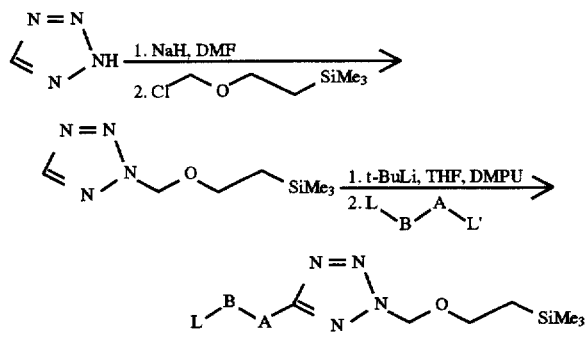

(3) Coupling of the electrophile and the heterocycle.

Coupling of the appropriate heterocycle and electrophile ms the next stage of the synthesis of compounds of formula 1. As shown below, treatment of compound 2, the heterocycle, with a suitable base, such as sodium hydride or cesium carbonate, in a suitable polar aprotic solvent, such as DMF, followed by the addition of sodium iodide and the electrophile 3 where L is a suitable leaving group, preferably bromide or mesylate, provides 4, an intermediate for the preparation of compound 1.

An example of an alternate preparation of a tetrazole containing electrophile is shown below. Coupling of a carboxylic acid with 3-aminopropionitrile followed by reaction with TMSN$_3$ and hydrolysis provides a tetrazole which can be protected and functionalized as before to give the desired electrophile.

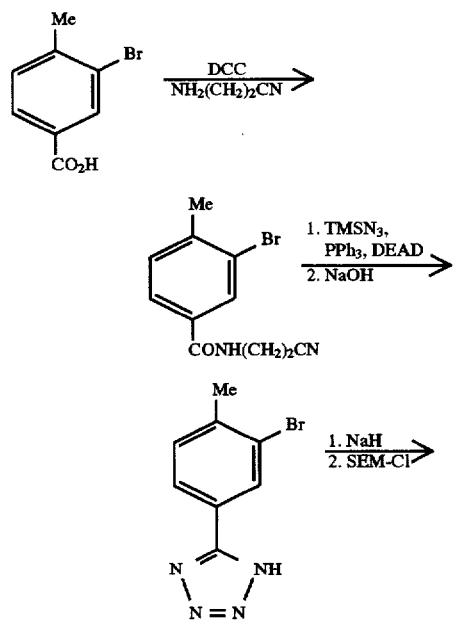

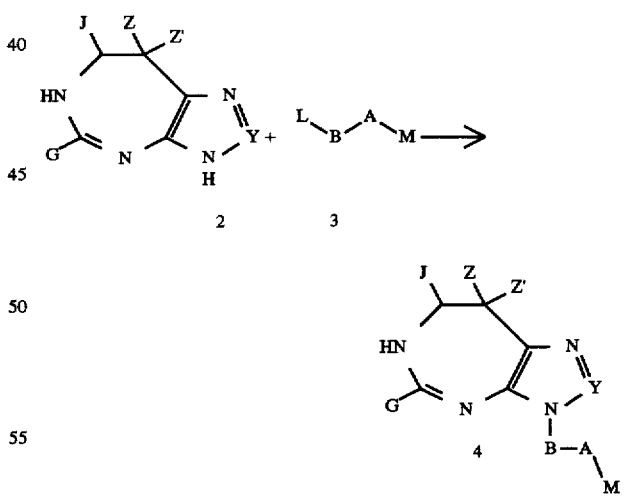

(4) Reduction of the C-8 ketone.

The C-8 ketone is preferably reduced after coupling the heterocycle and the electrophile. The reduction may be performed preferably with NaBH4 in a mixture of methanol and methylene chloride to provide the desired alcohol.

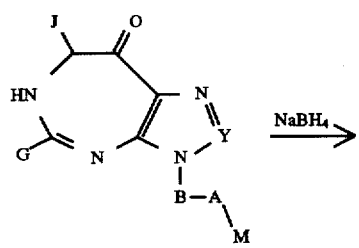

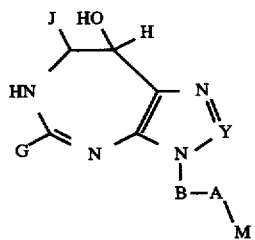

(5) Modification of the Coupled Molecule.

The coupled molecule may require further elaboration to provide desired compounds of formula 1, either before or after the reduction. The details of such modifications are described below.

Compounds of formula 1 where Z' is lower alkyl may be obtained as shown below. Protection of N-6 in the adduct is accomplished by deprotonation and alkylation with SEM-Cl. Alkyllithium or alkylmagnesium halide addition to the ketone inserts the Z' group. The synthesis of the desired molecule is completed by desilylation with TBAF.

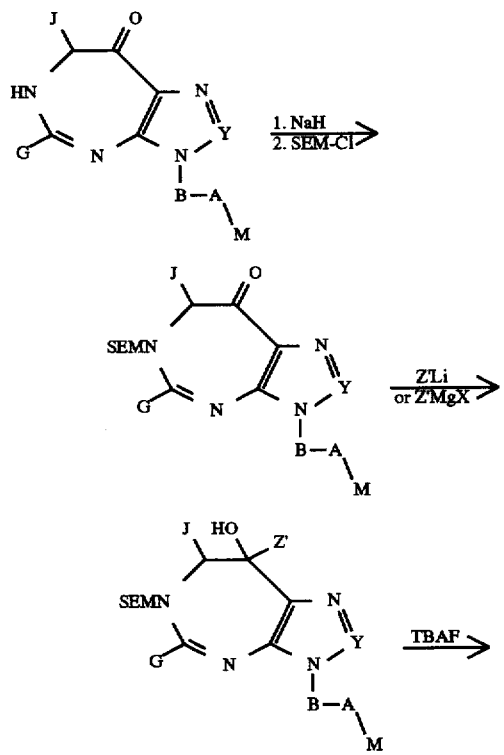

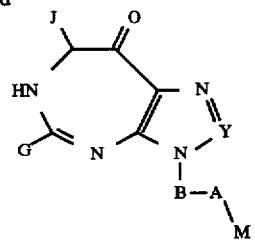

Compound 1 where X is amino may be prepared by Pd/C catalyzed hydrogenation of the compound where x is azido and the resultant amine converted to a guanidino function by treatment with aminoiminomethanesulfonic acid as shown below.

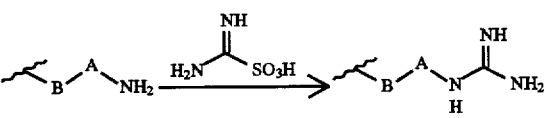

Compound 1 where X is OH or SH may be prepared by treatment of 4 where M is O-acyl or S-acyl, preferably acetate, with a hydrolytic agent, such as an alkoxide, preferably sodium methoxide in methanol.

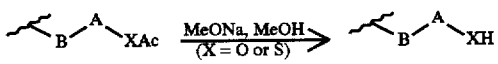

Compound 1 where X is $CO_2H$ is obtained by alkaline ester hydrolysis, preferably with aqueous NaOH, or by hydrogenolysis of a suitable benzyl (R=Bn) ester.

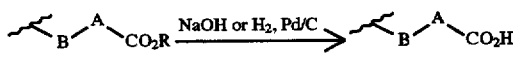

Compound 1 where X is $C(W)(CO_2R)(COQ)$, where W is H and Q is OH, may be obtained by hydrolysis of the tricarboalkoxy-methyl precursor with suitable base, such as aqueous NaOH.

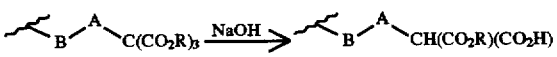

Compound 1 where X is $C(W)(CO_2H)(COQ)$ may be obtained by alkaline hydrolysis of an alkyl ester or hydrogenolysis of the appropriate benzyl ester.

Compound 1 where X is $C(W)(CO_2H)_2$ may be obtained preferably by hydrogenolysis of a dibenzyl ester (R=Bn) as shown below.

Compound 1 where X is $C(W)(CO_2R)(COQ)$, where Q is OR', SR' or $NR'_2$, may be obtained from the ester or amide forming reaction of the appropriate carboxylic acid with HOR', HSR' or $HNR'_2$ in the presence of a suitable coupling reagent, preferably diphenylphosphorylazide (DPPA) and triethylamine as shown below.

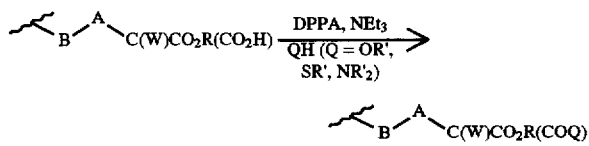

Compound 1 where X is C(O)NH$_2$ may be obtained by reaction of ammonia, with a suitable ester in a suitable solvent, for example ethanol, as below.

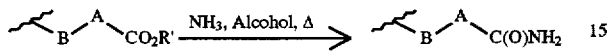

Compound 1 where X is C(O)NH-amino acid can be obtained by an amide forming reaction between a carboxylic acid and the amine terminus of an amino acid in the presence of suitable coupling reagents, such as N-hydroxysuccinimide (NHS) and dicyclohexylcarbodiimide (DCC) as shown below.

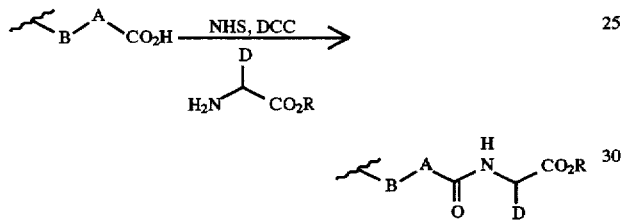

Compound 1 where X is a tetrazole can be obtained by treatment of an N-trimethylsilylethoxymethyl (SEM) protected tetrazole with fluoride, e.g.: CsF or tetrabutylammonium fluoride (TBAF), in DMF as shown below.

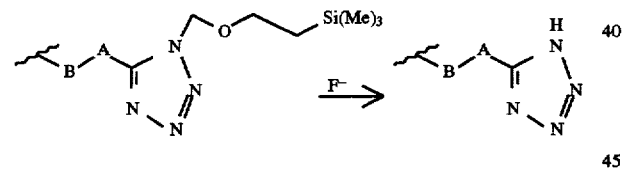

Compound 1 where X is P(O)(OR)OH can be obtained by hydrolysis of a phosphonate diester with a suitable base, such as lithium methoxide in methanol or aqueous NaOH as shown below.

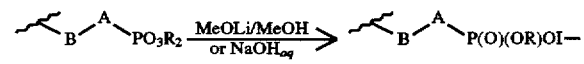

Compound 1 where X is PO$_3$H$_2$ can be obtained by hydrogenolysis of a suitable phosphonate as shown below.

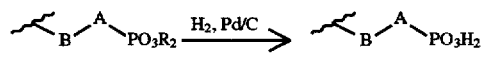

Compounds of formula 1 where Z is thiol or azide can be obtained as shown below. Treatment of the compound of formula with thioacetic acid acetylates N-6. The C-8 hydroxy is then converted to a thioacetate or azide group after which methanolic ammonia provides the desired thiol or azide. When Z is azide it may be converted to compounds where Z is amino by Pd/C catalyzed hydrogenation.

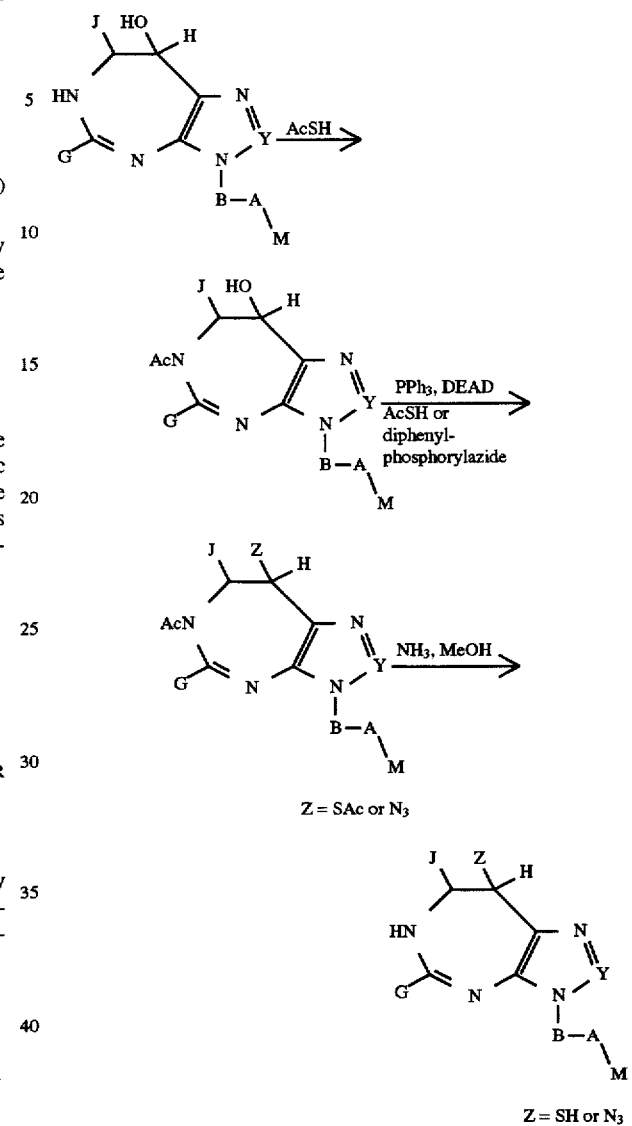

Compounds of formula 1 where Z is an acyloxy or a thioester group may be obtained as shown below. N-6 of the ketone is protected by alkylation with benzyloxymethyl chloride (BOM-Cl). Reduction of the ketone and conversion to an acetate or a thioacetate can be accomplished in the presence of PPh$_3$, DEAD and acetic or thioacetic acid. Deprotection of N-6 by hydrogenolysis provides the desired ester.

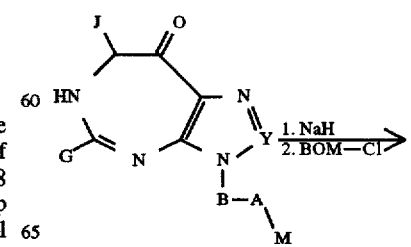

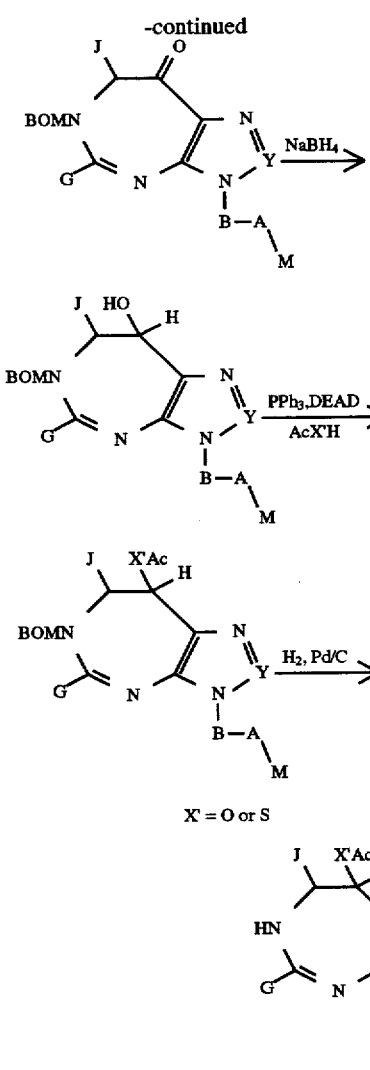

X' = O or S

The method described above for producing oxygen or sulfur derivatives at C8 may be employed for the chiral synthesis of analogs of compound 1. Preparation of suitable, chiral precursors is described above in "Preparation of the heterocycle." Treatment of the appropriate chiral alcohol with these conditions yields the chiral compound.

The preparation of other chiral analogs can be achieved by applying methods that are known to the art starting from the ketone, compound 4 where z and Z' are =O. For example, asymmetric reduction of the 8-keto group to the chiral alcohol can be achieved with reagents such as β-(3-pinanyl)-9-borabicyclo[3.3.1]nonane, chiral oxazaborolidines (CBS reduction), other reagents, or enzymatically with a reductase. An alternate method for obtaining chiral compounds is the resolution of the C8 alcohols enzymatically with a lipase. Furthermore, classical chemical methods for resolving stereochemical mixtures of alcohols and thiols via phthalates and oxalates and their alkaloid salts, or as a diastereomeric ester with a carboxylic acid such as camphoric acid, might be employed to generate the 8 R configuration.

An alternate preparation of compounds of formula 1 which does not fall within the above described 4-step route is shown below. The known styrenyl substituted derivative shown below is subjected to the alkylation procedure as described above to give compounds which may be processed in a manner described above to give compound 1.

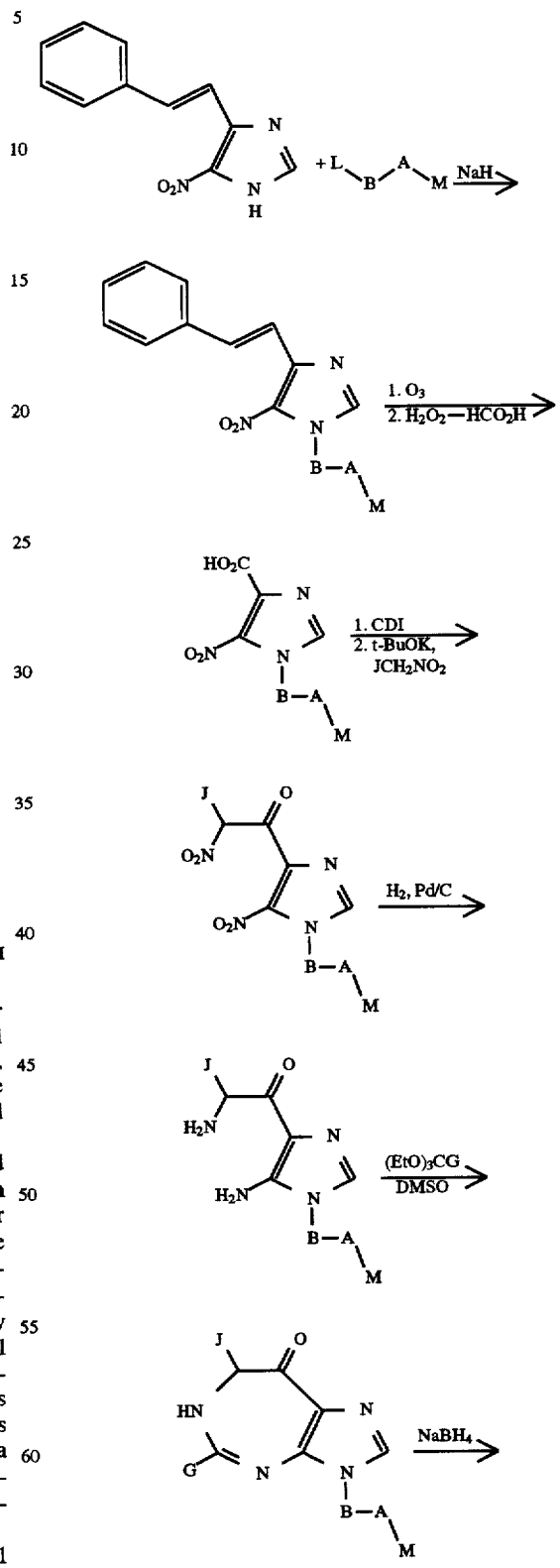

37
-continued

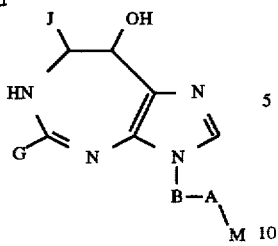

38
-continued

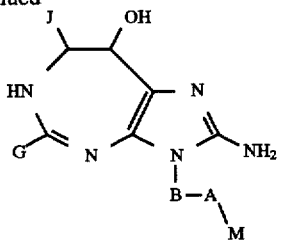

A modification of this route can be employed to prepare compounds of formula 1 where Y=C—K and K is Br, $N_3$ and $NH_2$ as shown below.

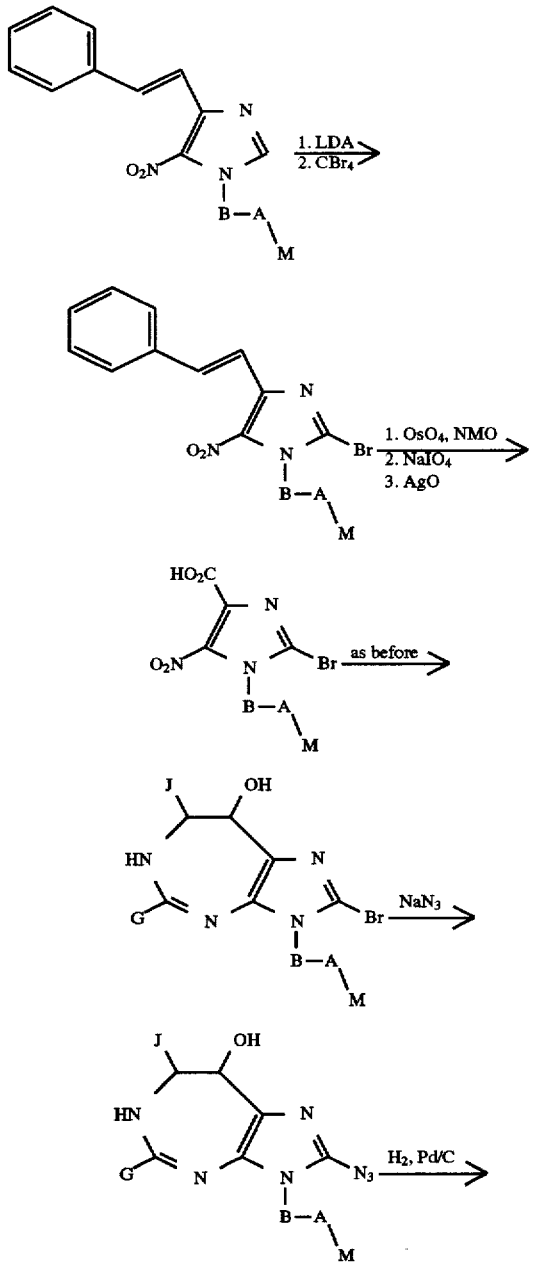

Utility

The adenosine monophosphate deaminase inhibitors of the present invention may be used in the treatment of a variety of clinical situations where increasing local levels of adenosine are beneficial. In particular, these compounds may be used in treating or preventing cardiovascular disorders in which injury or dysfunction is caused by ischemia and/or reperfusion (following a period of ischemia). These include (1) heart attack, a situation that arises from obstruction of one or more of the coronary arteries supplying blood to the heart muscle, and which, if prolonged, leads to irreversible tissue damage, especially during or after surgery; (2) angina pectoris, a clinical condition in which the blood supply to the heart is sufficient to meet the normal needs of the heart but insufficient when the needs of the heart increase (e.g. during exercise), and/or when the blood supply becomes more limited (e.g. during coronary artery spasm); (3) unstable angina associated with pain at rest; and (4) silent ischemia. In each of these conditions, treatment with AMP deaminase inhibitors will increase local levels of adenosine. Blood flow to the ischemic tissue would be increased, tissue damage reduced and function improved. Further, AMP deaminase inhibitors may also be used to treat or prevent congestive heart failure.

In advanced coronary artery disease or persistent chest pain at rest, a number of clinical procedures are currently used to improve blood supply to the heart. These include percutaneous transluminal coronary angioplasty (PTCA), percutaneous transluminal directional coronary atherectomy, laser atherectomy, intravascular stents and coronary artery bypass graft surgery. The compounds of the present invention will also be useful as adjunctive therapies to these techniques. Other clinical settings that involve ischemia would also be ameliorated by agents effecting regional blood flow including organ transplantation, skin flap grafting and other reconstructive surgery, peripheral vascular disease, endotoxemia, sepsis, toxic shock, hemorrhagic shock, pulmonary emboli, pulmonary injury secondary to burns (thermal injury) or septicemia, pulmonary hypertension, microembolization, glomerulonephritis or progressive glomerulosclerosis, atherosclerosis, myocarditis, vasculitis, cardiomyopathies, intestinal ischemia, peripheral vascular disease, transient ischemic attacks, stroke and cardiopulmonary arrest. Adenosine monophosphate deaminase inhibitors will enhance protection afforded by preconditioning a tissue with a brief period of ischemia, before a more prolonged period of ischemia.

Thrombolytic therapy has been limited by a number of factors including the resistance of some thrombi to lysis, delays in reperfusion, reperfusion injury, and reocclusion following successful thrombolysis. These limitations are believed to be mediated, in part, by platelet aggregation and neutrophil activation and, since adenosine inhibits platelet aggregation in addition to its other effects on preventing ischemic injury, use of these AMP deaminase inhibitors may comprise a useful adjunctive therapy for thrombolytic therapy or for the treatment or prevention of thrombotic diseases such as myocardial infarction, stroke, angina, deep vein thrombosis, restenosis, transient ischemic attacks, and pulmonary embolus.

Adenosine has been reported to be an endogenous modulator of inflammation by virtue of its effects on stimulated granulocyte function and on macrophage, lymphocyte and platelet function. AMP deaminase inhibitors, including the compounds of the present invention, may be useful in the treatment of disorders of the immune system, in particular inflammatory disorders and advantageously in the treatment of sepsis, septicemia or endotoxemia. Further, these compounds may be used in treating conditions such as arthritis, osteoarthritis, vasculitis, autoimmune disease, adult respiratory distress syndrome (ARDS), burns, pancreatitis, inflammatory bowel disease, necrotizing enterocolitis, chronic obstructive pulmonary disease (COPD), psoriasis, conjunctivitis, iridocyditis, myositis, cerebritis, meningitis, dermitis, renal inflammation, ischemia, reperfusion injury, peripheral vascular disease, atherosclerosis, AIDS and other inflammatory disorders.

Stroke and central nervous system ("CNS") trauma are conditions where tissue injury results from reduced blood supply to the CNS and are thus amenable to an intervention that provides increased levels of adenosine to the compromised tissue. A significant component of the neurodegeneration resulting from stroke or CNS trauma or neurodegenerative diseases may be caused by increased excitatory amino acid release and sensitivity, which results in neurons being stimulated to death. As adenosine has been reported to inhibit excitatory amino acid release (Burke and Nadler *J. Neurochem.*, 1988, 51:1541) and post-synaptic responses, compounds of this invention may be used in stroke and trauma and may also be used in the treatment of conditions such as Parkinson's disease, AIDS, Amyotrophic Lateral Sclerosis, Huntington's chorea or in the treatment of disorders related to the effects of aging such as Alzheimer's disease or in treating schizophrenia.

AMP deaminase inhibitors may also be useful in reducing anxiety, as skeletal muscle relaxants and in preventing skeletal muscle spasm.

Adenosine has been proposed to serve as a natural anticonvulsant, thus agents that enhance adenosine levels may be used in the treatment of seizure disorders. AMP deaminase inhibitors may be used in the treatment of patients prone to or inflicted with seizures or epilepsy or who might have chronic low or insufficient adenosine levels or might benefit from increased adenosine such as those suffering from autism, cerebral palsy, insomnia or other neuropsychiatric symptoms. Other excitatory neuromuscular tissues such as smooth muscle and cardiac muscle may be treated using these AMP deaminase inhibitors. In particular, these AMP deaminase inhibitors may be used to decrease contraction in smooth muscle such as in the gastrointestinal tract, or in vascular tissue such as an artery to prevent vasospasm which may limit blood supply to a tissue. Thus, these AMP deaminase inhibitors may be used to treat or prevent conditions such as Buerger's disease, Raynaud's disease, thromboangiitis obliterans, angina, unstable angina, silent ischemia, or transient ischemic attacks. Other conditions suitable for such therapy include cardiac arrhythmias (including supraventricular tachycardia), irritable bowel syndrome, and impotence.

AMP deaminase inhibitors find further utility in the treatment of chronic and acute pain when administered in a systemic or localized (e.g., intrathecal) fashion, for example in the treatment of acute pain including but not limited to pain caused by general trauma, surgical procedures or dental work. Oral administration may be useful in controlling chronic pain including but not limited to pain caused by arthritis, cancer, trigeminal neuralgia, multiple sclerosis, neuropathies such as those arising from diabetes and AIDS and in addition, lower back pain and phantom limb pain.

In general, compounds of the present invention need to inhibit AMPDA with a Ki of about 500 µM or less. Preferably they inhibit AMPDA with a Ki of about 10 µM or less. These tests are run in a manner similar to those described in Example A using purified or semi-purified enzyme extracts.

For certain indications compounds which are dual inhibitors of both AMP deaminase and ADA may be advantageous. Such compounds may have a synergistic activity due to inhibition of both enzymes and therefore would exhibit their desired therapeutic effect at lower doses and lower percent inhibition of each enzyme. For example, inhibition of AMPDA increases adenosine concentration to a level where ADA becomes important in adenosine metabolism, thus inhibition of both enzymes is synergistic. Also complete inhibition or nearly complete inhibition of either enzyme would not be necessary. Toxicities due to lack of functional enzyme have been reported for both AMPDA and ADA-deficient humans. Complete ADA deficiency results in severe combined immunodeficiency. Complete AMPDA deficiency is reported to result in mild muscle fatigue. Use of a compound which inhibits both AMPDA and ADA would give beneficial effects without complete inhibition of either enzyme and therefore the use of such compounds would not result in the toxicities reported for complete inhibition of either enzyme. Such compounds may be particularly suited for treatment of acute conditions.

AMPDA inhibitors having low activity as ADA inhibitors may be particularly suited for treatment of chronic conditions.

Selective AMP deaminase inhibitors or mixed AMP deaminase and ADA inhibitors will be useful in the treatment of infections, especially those caused by protozoa and worms. They will also be useful in combination with therapy which involves murine and/or pyrimidine metabolism. Such therapies include antivirals such as acylovir, azidothymidine, dideoxyinosine, adenosine arabinoside, dideoxyadenosine, ribovirin and cancer chemotherapies such as 5-fluorouracil, azathiopyrine, dacarbazine, cytosine arabinoside, methotrexate, brendinin, tiazafurin, 2'-deoxycoformycin and 2'-deoxy-2-chloroadenosine. The drugs of the present invention will also be useful in immunosuppressive, organ transplant, therapy.

Cancer cells and parasites, especially malaria, have special requirements for purines compared to mammalian cells. These special needs for purines have resulted in research directed to the discovery of agents which interfere with purine pathways. For example, methotrexate and 6-mercaptopurine for the treatment of cancer and allopurinol for the treatment of leischmania. Although we do not wish to be bound by this or any other theory, we believe that AMP deaminase inhibitors or mixed AMP deaminase and adenosine deaminase inhibitors will be useful for treating cancer and parasitic infections, especially malaria, by their ability to interrupt purine metabolism. We believe that by preventing AMP and adenosine deamination, the cancer cell or parasite will become starved for guanylates and become unviable.

To assist in understanding the present inventions and especially their properties and utilities, the results of a series of experiments are also included. These experiments demonstrated that a number of compounds of formula 1 were potent inhibitors of AMP deaminase. Moreover, we have shown that many of these compounds are specific inhibitors of AMP deaminase and inhibit adenosine deaminase (ADA) much less strongly.

In other experimental models, the ability of selected AMP deaminase inhibitors to inhibit neutrophil adherence to cardiomyocyte cells, an inflammatory response mediated at the cellular level was evaluated (Example C). Neutrophil adhesion, migration into the extravascular space and secretion of cytotoxic products such as oxygen free radicals and proteases as well as physical obstruction of capillaries by activated neutrophils have been reported as mechanisms by which neutrophils contribute to myocardial tissue injury, especially after ischemic tissue is perfused with oxygenated blood.

We have demonstrated the ability of these compounds to reduce damage resulting from ischemia and/or reperfusion in an experimental ischemic heart model as shown in Example D and in an experimental ischemic brain model as shown in Example F. Example F demonstrates the ability of these compounds to reduce infarct size. Further we have also demonstrated the ability of these compounds to prevent or treat neurologic disorders such as seizures as shown in Example E.

Formulations

Compounds of the invention are administered to the affected tissue at the rate of from 0.3 to 30 nmole/min/kg, preferably from 1 to 10 nmole/min/kg. Such rates are easily maintained when these compounds are intravenously administered as discussed below. When other methods are used (e.g., oral administration), use of time-release preparations to control the rate of release of the active ingredient may be preferred. These compounds are given in a dose of about 0.1 mg/kg/dose to about 30 mg/kg/dose, preferably from about 0.3 mg/kg/dose to about 10 mg/kg/dose.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of myocardial infarction. When an organ outside a body is being treated, perfusion is preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservative such as ethyl or n-propyl p-hydroxybenzoate, one or more coloring agent, one or more flavoring agent and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 200 μmoles of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion should contain from about 20 to about 50 μmoles of the active ingredient per milliliter of solution in order that infusion of a suitable volume at a rate of about 30 ml/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula 1 as such compounds are susceptible to acid hydrolysis.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of an adenosine monophosphate deaminase inhibitor compound.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Examples of use of the method of the invention includes the following. It will be understood that these examples are exemplary and that the method of the invention is not limited solely to these examples.

The method may be used following thrombolysis for coronary occlusion. The compound would be given as a sterile injectable preparation with water or isotonic sodium chloride as the solvent. The solution can be administered intravenously or directly into the coronary artery at the time of left heart catheterization or into a carotid artery. The rate of administration could vary from 1 to 20 nmole/min/kg with, for example, an infusion volume of 30 ml/hr. Duration of therapy would typically be about 96 hours.

Angina, early myocardial infarcts and other disorders where intravenous administration of drug may be preferable can be treated by using a sterile injectable preparation using the rates discussed above.

Capsules comprising adenosine monophosphate deaminase inhibitors suitable for oral administration according to the methods of the present invention may be prepared as follows: (1) for a 10,000 capsule preparation: 1500 g of adenosine monophosphate deaminase inhibitor is blended with other ingredients (as described above) and filled into capsules which are suitable for administration depending on dose, from about 1 capsules per day to about 8 capsules per day (2 capsules per 6 hours), to an adult human.

The compounds of this invention and their preparation can be understood further by the examples which illustrate some of the processes by which these compounds are prepared. These examples should not however be construed as specifically limiting the invention and variations of the invention, now known or later developed, are considered to fall within the scope of the present invention as herein after claimed.

EXAMPLES

Example 1
Preparation of the Electrophile.

1.0 mmol of an active hydrogen compound was treated with 1.1 mmol of NaH in 4 mL of DMF followed by addition of 1.5 mmol of the 1,ω-dibromoalkane. This mixture was stirred for 16 h. Extraction and chromatography provided the desired bromoalkyl electrophile.

The following compounds were prepared in this manner:
diethyl 2-(4'-bromobutyl)-2-methylmalonate as an oil,
dibenzyl 2-(4'-bromobutyl)-2-methylmalonate as an oil,
dimethyl 5-bromopentylphosphonate as an oil,
dimethyl 6-bromohexylphosphonate as an oil,
dibenzyl 5-bromopentylphosphonate as an oil and
dibenzyl 6-bromohexylphosphonate as an oil.

Example 2
Preparation of 5,5,5-Tricarbobenzyloxypentylbromide.

A mixture of 1 mmol of dibenzylmalonate and 2.5 mmol of NaH in 3 mL DMF was stirred at 0° C. for 1 h and then 1.5 mmol of CBz-Cl was added and stirring continued for 1.5 h at 0° C. Extraction and chromatography provided tricarbobenzyloxymethane as an oil.

A mixture of 1 mmol of this compound and 1.4 mmol of NaH in 10 mL of DMF was stirred at 0° C. for 1 h and then 2 mmol of 1,5-dibromopentane and stirring continued for 16 h at 90° C. Extraction and chromatography provided the title compound.

Example 3
Alternate Preparation of the Electrophile.

A mixture of 1 mmol of the active hydrogen compound, 2 mmol of $K_2CO_3$ and 1.5 mmol of 1,2-dibromoethane in 1 mL of DMSO was stirred for 4 h at rt. Extraction and chromatography provided the desired bromoalkyl electrophile.

The following compounds were prepared in this manner:
2-(p-carbomethoxyphenoxy)bromoethane as an oil and 2-(p-carbomethoxyphenylthio)bromoethane as an oil.

Example 4
Preparation of Methyl 2-(2'-Bromoethylmercapto)-3-isopropylbenzoate.

To a solution of 1.0 mmol 2-isopropylthiophenol and 2.2 mmol TMEDA in 2 mL cyclohexane was added 2.2 mmol n-BuLi. Then after stirring 24 h it was added to solid $CO_2$ and stirred for 16 h when extraction and chromatography provided 2-mercapto-3-isopropylbenzoic acid. The methyl ester of this was treated as in example 3 to provide the title compound.

Example 5
Preparation of 1-Bromo-3-mercaptoacetomethoxypropane.

A solution of 1 mmol ethyl mercapatoacetate, 1.25 mmol 1,3-dibromopropane and 1 mmol triethylamine in 2 mL ethanol was stirred for 16 h at rt. Extraction and chromatography provided the title compound as an oil.

Example 6
Preparation of n-Propyl Bromoethylmercaptopropionate.

A solution of 1.0 mmol of n-propyl 3-mercaptopropionate, 3.0 mmol of diisopropylethylamine and 3.0 mmol of 1,3-dibromopropane in 2 mL of toluene was refluxed for 3 h. Extraction and chromatography provided the title compound as an oil.

The following compound was prepared in the same manner: ethyl 1-(3'-bromopropyl)-2-piperidinecarboxylate as an oil.

Example 7
Preparation of 1-Bromo-2-(3'-carbomethoxyphenoxy)ethane.

A solution of 1 mmol methyl m-hydroxybenzoate, 2.3 mmol triphenylphosphine and 2.3 mmol 2-bromoethanol in 17 mL of THF was cooled to 0° C. and 2.3 mmol diethyl azodicarboxylate (DEAD) was added. The mixture was stirred at rt for 11 h. Chromatography provided the title compound as an oil.

Example 8
Preparation of Dimethyl N-(3-Bromopropyl)iminodiacetate.

A mixture of 1 mmol iminodiacetic acid dimethylester hydrochloride salt, 5 mmol N,N-diisopropyl-ethylamine and 3 mmol 1,3-dibromopropane in 2 mL toluene was stirred at 90° C. for 16 h and then chromatographed to provide the title compound as an oil.

Example 9
Preparation of Arylalkylbromides and Arylalkylmesylates.

A mixture of 1.0 mmol of aryl iodide (or triflate or bromide), 0.1 mmol of $Pd(PPh_3)_2Cl_2$, 0.05 mmol of CuI, 2.0 mmol of alkyne alcohol, and 4 mL base (diethylamine or triethylamine) was stirred until complete by tlc (3–72 h). Chromatographic purification provided the arylalkyne alcohol.

A mixture of 1.0 mmol of the arylalkyne, 0.1 mmol of 10% Pd/C in 5 mL EtOAc was hydrogenated and then filtered and concentrated to provide the arylalkanol.

A mixture Of 1.0 mmol of the arylalkanol, 1.2 mmol of $PPh_3$, 1.2 mmol of $CBr_4$, and optionally 1.2 mmol of imidazole in 3 mL of $CH_2Cl_2$ was stirred for 5 min. and then chromatographed to provide the title arylalkylbromide.

Alternatively, 1.0 mmol of the arylalkanol was mixed with 1.5 mmol MsCl and 1.5 mmol triethylamine in $CH_2Cl_2$ for 1 h and then extractive isolation provided the title arylalkylmesylate.

The following compounds were prepared in this manner:
2-(3'-bromopropyl)toluene as an oil,
2-(3'-bromopropyl)trifluoromethylbenzene as an oil,
2-(3'-bromopropyl)-1,5-dimethylbenzene as an oil,
2-(3'-bromopropyl)-1,4-dimethylbenzene as an oil,
2-(3'-bromopropyl)mesitylene as an oil,
2-(3'-bromopropyl)-3-methylthiophene as an oil,
3-(4'-propylphenyl)propane mesylate as an oil,
6-(2'-bromophenyl)hexyl mesylate as an oil,
methyl 3-(3'-bromopropyl)benzoate as an oil,
methyl 3-(3'-bromopropyl)-4-methoxybenzoate as an oil,
methyl 2-(3'-bromopropyl)benzoate as an oil,
methyl 2-fluoro-6-(3'-bromopropyl)benzoate as an oil,
methyl 5-(3'-bromopropyl)furan-2-carboxylate as an oil,
methyl 3-(3'-bromopropyl)thiophene-2-carboxylate as an oil,
methyl 2-(3'-bromopropyl-3-isopropylbenzoate as an oil,
methyl 2-(3'-bromopropyl-3-isopropyl-6-methylbenzoate as an oil,
methyl 2-(3'-bromopropyl-4-methylbenzoate as an oil,
methyl 2-(3'-bromopropyl)-5-methylbenzoate as an oil and
methyl 1-(3'-bromopropyl)-2-napthalene-2-carboxylate as an oil.

Example 10
Preparation of N-Methyl-(3-(3'-bromopropyl)-4-methylphenyl)-carboxamide.

A solution of 1.0 mmol of 3-iodo-4-methylbenzoic acid, 1.2 mmol of TsCl, and 25 mmol of Py was stirred for 3 h and then 5 mmol of methylamine hydrochloride was added and stirring continued for 5 h. Chromatography provided N-methyl-(3-iodo-4-methylphenyl)carboxamide.

This compound was coupled with propargyl alcohol, hydrogenated and converted to the title bromide as an oil by methods previously described.

Example 11
Alternate Preparation of Arylpropyl Mesylates.

A solution of 1 mmol of a cinnamic acid in 2 mL THF was added slowly to 2 mL of a 1M solution of LiAlH$^4$ in THF at 0 ° C. After 2 h stirring at rt extractive isolation provided a residue which was optionally subjected to hydrogenation in methanol over 10% Pd/C. Filtration and evaporation provided the arylpropyl alcohol and this was mesylated as previously described.

The following compounds were prepared in this manner:
3-(2'-chlorophenyl)propyl mesylate as an oil,
3-(3'-chlorophenyl)propyl mesylate as an oil,
3-(4'-chlorophenyl)propyl mesylate as an oil,
3-(2'-bromophenyl)propyl mesylate as an oil,
3-(3'-bromophenyl)propyl mesylate as an oil,
3-(4'-bromophenyl)propyl mesylate as an oil,
3-(2'-ethoxyphenyl)propyl mesylate as an oil,
3-(3'-ethoxyphenyl)propyl mesylate as an oil,
3-(4'-ethoxyphenyl)propyl mesylate as an oil,
3-(4'-methoxyphenyl)propyl mesylate as an oil,
3-(4'-trifluoromethoxyphenyl)propyl mesylate as an oil,
3-(4'-isopropylphenyl)propyl mesylate as an oil and
3-(biphenyl-4'-yl)propyl mesylate as an oil.

Example 12
Alternate Preparation of Alkoxyarylpropyl mesylates.

A mixture of 1 mmol of a hydroxycinnamic acid, 2.1 mmol alkyl bromide (or iodide)and 2.1 mmol $K_2CO_3$ in 4 mL of DMF was heated at 80° C. for 6 h and then extractive isolation provided the alkyl alkoxycinnamate and this compound was reduced and mesylated as before to provide the title compound.

The following compounds were prepared in this manner:
3-(2'-benzyloxyphenyl)propyl mesylate as an oil,
3-(3'-benzyloxyphenyl)propyl mesylate as an oil,
3-(4'-benzyloxyphenyl)propyl mesylate as an oil,
3-(4'-propoxyphenyl)propyl mesylate as an oil and
3-(4'-butoxyphenyl)propyl mesylate as an oil.

Example 13
Preparation of Bromoethylthiophenyl Carboxylates.

A solution of 1.0 mmol of hydroxyethylthiophene, 5.0 mmol imidazole, 0.1 mmol DMAP and 1.2 mmol TBDMSCl in 4 mL of DMF was stirred for 6 h. Extraction and chromatography provided the TBDMS ether.

To a solution of 1.0 mmol of this thiophene in 2 mL of THF was added 1.2 mmol of n-BuLi at −78° C. After 5 h an alkyl chloroformate was added. Extraction and chromatography provided an ester.

A solution of 1.0 mmol of this ester and 1.5 mmol of TBAF in 2 mL of THF was stirred at 0° C. for 12 h. Extraction and chromatography to provided a hydroxyethylthiophene which was converted to the title bromide by previously described method.

The following compounds were prepared in this manner:
benzyl 5-(2'-bromoethyl)thiophenyl-2-carboxylate as an oil and
methyl 4-(2'-bromoethyl)thiophenyl-2-carboxylate as an oil.

Example 14
Preparation of N-(3-Mesyloxypropyl)-N-formylphenylalanine Methyl Esters.

To a mixture of 1 mmol of phenylalanine methyl ester hydrochloride and 2 mmol of triethylamine in 1 mL of DMF at 0 ° C. was added 2 mL of formic acid and 0.7 mL of acetic anhydride. After stirring for 16 h at rt, extractive isolation provided N-formylphenylalanine methyl ester.

A mixture Of 1 mmol of this compound and 1.2 mmol of NaH in 10 mL DMF at 0° C. was stirred for 1 h and then 1.2 mmol of 3-t-butyldimethylsilyloxypropylbromide was added and stirring continued for 16 h at rt. Extraction and chromatography provided an adduct which after treatment with TBAF and then mesylation of the resultant alcohol by methods previously described provided the title compound.

The following compounds were prepared in this manner:
N-(3-mesyloxypropyl)-N-formyl-L-phenylalanine methyl ester as an oil and
N-(3-Mesyloxypropyl)-N-formyl-D-phenylalanine methyl ester as an oil.

Example 15
Preparation of Ethyl 2-Benzyl-6-mesyloxyhexanoates.

A solution of 1 mmol of caprolactone in 0.5 mL THF was added to a solution of LDA in 0.5 mL THF at −78° C. and this stirred for 2 h. Then a solution of 1.1 mmol of a benzylbromide in 0.14 mL DMPU was added to the above mixture and after stirring for 1 h at −15° C., the 2-benzylcaprolactone was isolated by extraction and chromatography.

A mixture of 1 mmol of this lactone and 1 mmol of Al(OEt)3 was refluxed in toluene for 14 h. Extraction and chromatograpy provided an ethyl 2-benzyl-6-hydroxyhexanoate which was converted to a title mesylate by previously described methods.

The following compounds were prepared in this manner:
ethyl 2-benzyl-6-mesyloxyhexanoate as an oil,
ethyl 2-(2'-bromobenzyl)-6-mesyloxyhexanoate as an oil,
ethyl 2-(3'-bromobenzyl)-6-mesyloxyhexanoate as an oil and
ethyl 2-(4'-bromobenzyl)-6-mesyloxyhexanoate as an oil.

Example 16
Preparation of 2-(2'-Isopropyl-5'-methylcyclohexyloxy) ethyl bromides.

A mixture of 1 mmol of a menthol and 1.1 mmol of NaH was stirred in DMF for 1 h followed by the addition of 1.3 mmol bromoethyl-m-butyldimethylsilyl ether and stirring at 60° C. for 16 h. Extraction and chromatography provided the adduct.

This adduct was desilyated with TBAF and converted to the title bromide by previously described methods.

The following compounds were prepared in this manner:
(1'R,2'S,5'R)-2-(2'-isopropyl-5'-methylcyclohexyloxy)ethyl bromide as an oil and
(1'S,2'R,5'S)-2-(2'-isopropyl-5'-methylcyclohexyloxy)ethyl bromide as an oil.

Example 17
Preparation of Ethyl 3-Bromo-4-(hydroxymethyl)benzoate TBDMS ether.

A mixture of 1.0 mmol of ethyl 3-bromo-4-methylbenzoate, 1.0 mmol NBS, and 0.02 mmol benzoyl peroxide in 5 mL $CCl_4$ was refluxed for 4 h and then processed by filtration and chromatography to provide ethyl 3-bromo-4-bromomethylbenzoate as an oil.

A mixture of 1.0 mmol of this compound in 3 mL of dioxane and 5.0 mmol of $CaCO_3$ in 6 mL of $H_2O$ was stirred for 12 h at 100° C. and then processed by chromatography to provide 3-bromo-4-hydroxymethylbenzoic acid as solid.

Silylation of this compound was performed as previously described and esterification by standard conditions provided the title compound as an oil.

Example 18
Preparation of Alkyl 3-(2'-bromoethyl)benzoates.

A mixture of 1.0 mmol of an alkyl 3-bromobenzoate, 1.5 mmol allyltributyltin, and 0.1 mmol $Pd(PPh_3)_4$ in 4 mL DMF was stirred at 90° C. for 1–16 h and then chromatographed to provide an alkyl 3-allylbenzoate.

Ozone was passed into a solution of 1.0 mmol of this allyl derivative in 10 mL of MeOH at −78° C. until blue. Nitrogen degassing was followed by addition of 5 mmol of $NaBH_4$ and after stirring for 1 h the mixture was processed by chromatography to provide an alkyl 3-(2'-hydroxyethyl)benzoate which was converted to the title compound by a previously described method.

The following compounds were prepared in this manner: methyl 3-(2'-bromoethyl)benzoate as an oil, benzyl 3-(2'-bromoethyl)-4-methylbenzoate as an oil, methyl 3-(2'-bromoethyl)-4-methylbenzoate as an oil, ethyl 3-(2'-bromoethyl)-4-methylbenzoate as an oil,
methyl 3-(2'-bromoethyl)-4-methoxybenzoate as an oil, ethyl 3-(2'-bromoethyl)-4-fluorobenzoate as an oil and ethyl 3-(2'-bromoethyl)-4-(t-butyldimethylsilyloxymethyl) benzoate as a deliquescent solid.

Example 19
Preparation of Ethyl 3-(2'-bromoethyl)-5-bromobenzoate.

A mixture of 1.0 mmol of the ethyl 3-allyl-5-bromobenzoate (prepared as previously described), 0.1 mmol of $RuO_2$, 2.5 mmol of $NaIO_4$, 4 mL of $CCl_4$, 6 mL of $H_2O$ and 4 mL of $CH_3CN$ was stirred for 15 min. Then it was extracted and treated with 10 mmol of NaBH4 in 2 mL of MeOH to produce an alcohol which was converted to the title bromide by a previously described method.

Example 20
Preparation of Ethyl 3-(Bromomethyl)phenylacetate.

A mixture of 1.0 mmol of ethyl 3-bromophenylacetate, 1.5 mmol of vinyltributyltin, and 0.1 mmol of $Pd(PPh_3)_4$ in 4 mL DMF was stirred and heated at 90° C. for 1–16 h. Chromatography provided ethyl 3-vinylphenylacetate.

A solution of 1.0 mmol of this olefin, 0.2 mmol of $OsO_4$, 1.2 mmol of NMO, 3 mL of t-BuOH, 3 mL of $H_2O$ and 7 mL of THF was stirred for 3 h and then after the addition of 12.0 mmol of $NaHCO_3$, 15 mL of $H_2O$ and 3.0 mmol of $NaIO_4$ the mixture was stirred for 45 min. Extraction and chromatography provided the aldehyde.

A solution of 1.0 mmol of this aldehyde and 1.0 mmol of $NaBH_4$ in 2 mL of MeOH was stirred for 1 h. Chromatography provided ethyl 3-(2'-hydroxyethyl)-5-bromobenzoate as an oil.

This compound was converted to the title compound by a previously described method.

Example 21
Preparation of 5-Substituted Ethyl 3-(2'-bromoethyl)benzoates.

A mixture of 1.0 mmol of ethyl 3-(2'-hydroxyethyl)-5-bromobenzoate, 0.1 mmol of $Pd(Ph_3)4$, 1.5 mmol of a phenylboronic acid or 1.5 mmol of a vinyltributyltin, 3.0 mmol of $K_2CO_3$, 3 mL of diglyme and 1 mL of $H_2O$ was heated at 90° C. for 12 h. Chromatography provided a compound which was converted to the title bromide by a previously described method.

The following compounds were prepared in this manner: ethyl 3-(2'-bromoethyl)-5-phenylbenzoate as an oil and ethyl 3-(2'-bromoethyl)-5-ethylbenzoate as an oil from hydrogenation of the 5-vinyl derivative.

Example 22
Ethyl 2-methyl-5-(2'-bromoethyl)benzoate.

A mixture of 1.0 mmol of 3-iodo-4-methylbenzoic acid and 1.2 mmol of NaBH4 in 4 mL of anhydrous THF was stirred for 30 min and then 0.5 mmol of iodine in 2.0 mL of THF at 5° C. was added. After stirring for 2 h the mixture was processed by extraction to provide 3-iodo-4-methylbenzyl alcohol.

A mixture of 1.0 mmol of this alcohol and 5.0 mmol of $MnO_2$ in 5 mL of $CH_2Cl_2$ was stirred for 16 h at rt. Chromatography provided 3-iodo-4-methylbenzaldehyde.

This aldehyde (1 mmol)was added to a premixed solution of 1.5 mmol of methyl triphenylphosphonium bromide and 1.2 mmol of n-BuLi in 5 mL of THF at 0° C. and this mixture was stirred for 3–6 h at rt and then processed by extraction and chromatography to give 3-iodo-4-methylstyrene.

To a solution of 1 mmol of this iodide in 4 mL of THF was added 1.2 mmol of BuLi and after stirring for 1 h at −78° C., ethyl chloroformate was added. Extraction and chromatography provided ethyl 2-methyl-5-vinylbenzoate.

1.0 mmol of this styrene derivative in 4 mL of THF was treated with 2.0 mmol of 9-BBN in THF and after stirring for 30 h and cooling to 0° C., 4.0 mmol of 30% hydrogen peroxide followed by 2.1 mmol of 3N NaOH was added. After stirring for 10 h the mixture was processed by extraction and chromatography to provide ethyl 2-methyl-5-(2'-hydroxyethyl)benzoate.

This alcohol was converted by a previously described method to the title compound as an oil.

Example 23
Preparation of Methyl 2-Fluoro-5-(2'bromoethyl)benzoate.

A mixture of 1.0 mmol of 3-bromo-4-fluorobenzaldehyde, 4 mL of DMF, 0.2 mL of triethylamine, 0.4 mL of MeOH and 0.05 mmol of $Pd(PPh_3)_4$ was heated at 90° C. at 40 psi under CO atmosphere for 16 h. Extraction and chromatography provided methyl 3-carbomethoxy-4-fluorobenzaldehyde.

This aldehyde was treated as previously described to provide the title compound as an oil.

Example 24
Preparation of Methyl 4-(2'-Bromoethyl)-2-naphthoate.

The compound 4-bromo-2-naphthoic acid was prepared according to the method of Adcock and Wells, *Aust. J. Chem.* 1965, 18, 1351. It was converted to its methyl ester by standard methods.

This naphthylbromide was cross coupled with vinyl stannane, the resulting naphthylvinyl compound subjected to hydroboration/oxidation and the resulting alcohol converted to the title compound as an oil all by previously described methods.

Example 25
Preparation of 2-Bromomethyl-cis-(2'-carbomethoxyethyl)-cyclohexane.

A mixture of 1 mmol of 1,2-cis-cyclohexane dimethanol, 10 mL of $CH_2Cl_2$, 0.4 g of molecular sieves (4 angstroms) and 3.0 mmol of PCC was stirred for 3 h. Chromatography provided cis-1,2-hexahydrocoumaranone as an oil.

A solution of 1.0 mmol of this cyclohexyllactone in 1 mL of toluene and 1.02 mmol of DIBALH at −78° C. was stirred for 2 h. Extraction and chromatography provided a lactol as an oil.

1 mMol of this lactol in 2 mL $CH_3CN$ was added to a premixed suspension of 2.0 mmol of NaH and 3.0 mmol of carbomethoxymethyltriphenylphosphonium bromide in 2 mL of $CH_3CN$ at 0° C. and then the mixture was stirred for 5 h at 80° C. Extraction and chromatography provided methyl cis-(2'-hydroxymethylcyclohexyl)-2-acrylate as an oil.

This ester was hydrogenated and converted to the title bromide as an oil by previously described methods.

Example 26
Preparation of Methyl trans-4-Bromomethylcyclohexane Carboxylate.

1,4-trans-cyclohexane dimethanol was converted to trans-4-Bromomethylcyclohexane methanol by previously described methods.

A solution of 1.0 mmol of this alcohol and 5.0 mmol of PDC in 10 mL of DMF was stirred at rt for 36 h. Extraction and chromatography provided a carboxylic acid which was converted to the title ester by a standard procedure.

Example 27
Preparation of 4-Substituted Methyl 3-(2'-Bromoethyl) benzoates.

A mixture of 1.0 mmol of methyl 4-hydroxybenzoate, 2.0 mmol of allyl bromide, 5.0 mmol of $K_2CO_3$ in 2 mL of acetone was stirred for 16 h. Extraction provided methyl 4-allyloxybenzoate.

A solution of 1.0 mmol of this allylether, 1.0 mmol of BC13 in 5 mL of chlorobenzene was stirred 6 h at rt. Extraction provided 2-allyl-4-carbomethoxyphenol.

This compound was subjected to ozonolysis and TBDMS ether formation by previously described methods to provide 2-(2'-t-butyldimethylsiloxyethyl)-4-carbomethoxyphenol.

A solution of 1.0 mmol of this phenol, 6.0 mmol of triethylamine, and 2.4 mmol of Tf20 in 4 mL of THF was stirred at −78° C. for 1 h, then concentrated and dissolved in 4 mL of DMF. To this was added 0.15 mmol of Pd(PPh$_3$)$_2$Cl$_2$, 0.4 mmol of PPh$_3$, 8.0 mmol of LiCl, and 2 mmol of vinyl or allyl tributyltin and the mixture heated at 90° C. for 14 h. Extraction and chromatography provided the methyl 4-substituted-3-(2'-t-butyldimethylsiloxyethyl)benzoate.

After hydrogenation by a previously described method, a solution of 1.0 mmol of the resulting protected alcohol, 0.1 mmol of CSA in 1 mL of MeOH and 1 mL of $CH_2Cl_2$ was stirred for 10 h. Extraction and chromatography provided an alcohol which was converted to the title bromide by a previously described method.

The following compounds were prepared in this manner: methyl 3-(2'-bromoethyl)-4-ethylbenzoate as an oil and methyl 3-(2'-bromoethyl)-4-propylbenzoate as an oil.

Example 28
Preparation of 1-Bromo-2r(2'-Carboethoxycyclopropyl) ethane.

Ethyl diazoacetate (1.3 mmol) was added over 18 hours to a solution of 1.0 mmol 4-bromo-1-butene and 2 mg dirhodium tetraacetate in 10 mL of $CH_2Cl_2$. The solution was concentrated, filtered through silica, and fractionally distilled to give the title compound as an oil.

Example 29
Preparation of 5-(5'-Bromopentyl)-2-trimethylsilylethoxymethyltetrazole.

To a Suspension of 1.1 mmol NaH in 5 mL DMF at 0° C. was added a solution of 1.0 mmol tetrazole in 2 mL DMF. After 30 min, trimethylsilylethoxymethylchloride was added and the mixture stirred for 16 h. Extraction and chromatography provided trimethylsilylethoxymethyltetrazole as an oil.

To a solution of 1.0 mmol of this tetrazole in 4 mL of THF and 4 mL of 1,3-dimethyl-3,4,5,6-tetrahydro-2(1H) pyrimidinone at −78° C. was added 1.5 mL of 1.7M t-butyllithium in pentane. After 5 min, 5 mmol of 1,5-dibromopentane was added and the solution warmed to −22° C. and stirred for 7 h. Extraction and chromatography provided the title compound as an oil.

Example 30
Preparation of N-Trimethylsilylethoxymethyl-5-(3'-(2''-tosyloxyethyl)-4'-methylphenyl)tetrazole.

A mixture of 1.0 mmol of 3-bromo-4-methylbenzoic acid, 1.2 mmol of DCC, 1.0 mmol of 3-aminopropionitrile in 2 mL of DMF was stirred for 36 h at 0° C. Chromatography provided N-(3-cyanopropyl)-(3'-bromo-4'-methylphenyl) carboxamide.

A solution of 1.0 mmol of this amide, 4.0 mmol of TMSN3, 4.0 mmol of PPh$_3$, and 4.0 mmol of DEAD in 4 mL of THF at 0° C. was stirred 24 h and then concentrated. The residue was mixed with 5 mL of THF and 12.0 mmol of 1N NaOH. After stirring for 24 h and processing by extraction, 5-(3'-bromo-4'-methylphenyl)tetrazole was obtained.

A solution of 1.0 mmol of this tetrazole, 2.0 mmol of SEMCl in 10 mL DMF was stirred for 1 h. 2.0 mmol of allyltributyltin and 0.1 mmol of Pd(Ph3)$_4$ was added and heated at 70° C. for 14 h. Chromatography provided N-trimethylsilylethoxymethyl-5-(3'-allyl-4'-methylphenyl) tetrazole.

This compound was ozonized and converted to the title rosylate by methods described previously.

Example 31
Preparation of 6,7-Dihydroimidazo[4,5-d][1,3]diazepin-8 (3H)-one.

A suspension of 10 g of 6,7-dihydroimidazo-[4,5-d][1,3] diazepin-8(3H)-one hydrochloride DMSO solvate (prepared by the method of Chan, et al., *J. Org. Chem.* 1982, 47, 3457–3464) in 50 mL triethylamine was stirred for 30 min., 500 mL $CH_2Cl_2$ was added, the mixture stirred for 10 min and filtered. The solid was collected and washed with $CH_2Cl_2$ to provide the title compound: mp 260° C.

Example 31
Preparation of 6,7-Dihydro-5-methylimidazo[4,5-d][1,3] diazepin-8(3H)-one.

The compound 6,7-dihydro-5-methylimidazo[4,5-d][1,3] diazepin-8(3H)-one hydrochloride (prepared by the method of Showalter, et al., *J. Med. Chem.* 1983, 26, 1478)was converted to its freebase, the title compound, by a previously described method.

Example 32
Preparation of 6'7-Dihydro-7-methylimidazo[4,5-d][1,3] diazepin-8(3H)-one.

A mixture of 1 mmol of 1-benzyl-5-nitro-1H-imidazole-4-carboxylic acid (prepared by the method of Chan, et al., *J. Org. Chem.* 1982, 47, 3457–3464)and 1.25 mmol of carbonyldiimidazole in 2 mL of THF was refluxed for 30 min and then cooled to 0° C. and added to a premixed suspension of 4 mmol of nitroethane and 1.5 mmol of potassium t-butoxide in 1.5 mL of THF at 0° C. After stirring for 6 h at rt, extraction provided 2-nitro-1-(1'-benzyl-5'-nitro-1'H-imidazol-4'-yl)propanone as an oil.

A mixture of 1 mmol of this compound and 20 mg of palladium hydroxide on carbon in 5 mL of water adjusted to pH 2 with HCl was subjected to 45 psi $H_2$ for 2 h and then filtration and evaporation provided 2-amino-1-(5'-amino-1'H-imidazol-4'-yl)propanone dihydrochloride as a deliquescent solid.

A mixture of 1 mmol of this compound and 4 mmol of triethylorthoformate in 4 mL of ethanol was refluxed for 2 h and then concentrated and collected by filtration. The solid collected was freebased by a previously described method to provide the title compound as a deliquescent solid.

Example 33

General Procedure for Alkylation Of 6,7-Dihydroimidazo[4,5-d][1,3]diazepin-8(3H)-one end Reduction to the 3-Alkylcoformycin Aglycone Derivative.

A suspension of 1.1 mmol sodium hydride and 1 mmol of 6,7-dihydroimidazo[4,5-d][1,3]diazepin-8(3H)-one in 10 mL DMF was stirred at rt for 0.5 h. Then 1 mmol of the electrophile and 0.25 mmol of NaI were added and the mixture heated at 80 ° C. for 1 h. Chromatography provided the 3-alkyl-8-ketocoformycin aglycone derivative.

To a solution of this derivative (1 mmol)in 3 mL of 1:1 $CH_2Cl_2$:methanol was added 1 mmol $NaBH_4$ and the mixture stirred for 30 min. Chromatography provided the 3-alkylcoformycin aglycone derivative.

The following compounds were prepared in this manner:

3-(3'-carboethoxypropyl)coformycin aglycone, mp 109°–112° C.;

3-(3'-carbobenzyloxypropyl)coformycin aglycone, mp 116≧–117° C.;

3-(4'-carbomethoxybutyl)coformycin aglycone, mp 136°–139° C.;

3-(5'-carboethoxypentyl)coformycin aglycone, mp 115°–118° C.;

3-(6'-carboethoxyhexyl)coformycin aglycone, mp 117°–118° C.;

3-(7'-carbomethoxyheptyl)coformycin aglycone, mp 131°–133° C.;

3-(5'-carboethoxy-6'-phenylhexyl)coformycin aglycone, mp 121°–124° C.;

3-(5'-carboethoxy-6'-(2"-bromophenyl)hexyl)coformycin aglycone, mp 122°–125° C.;

3-<5'-carboethoxy-6'-3"-bromophenyl)hexyl)coformycin aglycone, mp 125°–127° C.;

3-(5'-carboethoxy-6'-(4"-bromophenyl)hexyl)coformycin aglycone, mp 114°–116° C.;

N-(3-(3',6',7',8'-tetrahydroimidazo[4',5'-d]-[1',3']diazepin-8'-ol-3'-yl)propyl)-N-formyl-D-phenylalanine methyl ester as a deliquescent solid;

N-(3-(3',6',7',8'-tetrahydroimidazo[4',5'-d]-[1',3']diazepin-8'-ol-3'-yl)propyl)-N-formyl-L-phenylalanine methyl ester as a deliquescent solid;

3-(5',5'-dicarboethoxyhexyl)coformycin aglycone, mp 122°–125° C.;

3-(5',5'-dicarbobenzyloxyhexyl)coformycin aglycone, mp 113°–116° C.;

3-(5',5',5'-tricarbobenzyloxypentyl)coformycin aglycone as a deliquescent solid;

3-(2'-(2"-carboethoxycyclopropyl)ethyl)coformycin aglycone cyclopropane isomers, mp 80°–88° C.;

3-(4'-carbomethoxybenzyl)coformycin aglycone, mp 185°–186° C.;

3-(4'-carbomethoxymethylbenzyl)coformycin aglycone, mp 170°–171° C.;

3-(3'-carboethoxymethylbenzyl)coformycin aglycone, mp 119° C.;

3-(2'-(2"-carbomethoxyphenoxy ethyl)coformycin aglycone, mp 180°–181° C.;

3-(4'-carbomethoxyphenylethyl)coformycin aglycone, mp 188°–189° C.

3-(2'-(2"-carbomethoxyphenylthio)ethyl)coformycin aglycone, mp 179°–180° C.;

3-(2'-(2"-carbomethoxy-6"-isopropylphenylthio)ethyl) coformycin aglycone, mp 154° C.;

3-(3'-(2"-carbomethoxyphenyl)propyl)coformycin aglycone, mp 144° C.;

3-(3'-(2"-carbomethoxynaphthyl)propyl)coformycin aglycone, mp 98°–100°C.;

3-(2'-(3"-carbomethoxynaphthyl)ethyl)coformycin aglycone, mp 238° C.;

3-(cis-2'-(carbomethoxyethyl)cyclohexylmethyl) coformycin aglycone, mp 135°–140° C.;

3-(3'-(3"-carbomethoxyphenyl)propyl)coformycin aglycone, mp 140°–145° C.;

3-(3'-carbomethoxyphenylmethyl)coformycin aglycone, mp 205°–207° C.;

3-(3'-(3"-carbomethoxy-6-methylphenyl)propyl) coformycin aglycone, mp 165°–168° C.

3-(3'-(3-N-methylcarboxamido-6"-methylphenyl)propyl) coformycin aglycone, mp 205° C.;

3-(3'-(2"-carbomethoxy-5"-methylphenyl)propyl) coformycin aglycone, mp 165°–170° C.;

3-(3'-(2"-carbomethoxy-4"-methylphenyl)propyl) coformycin aglycone, mp 144° C.;

3-(3'-(2"-carbomethoxy-3"-fluorophenyl)propyl) coformycin aglycone, mp 131° C.;

3-(2'-(3"-carboethoxy-5"-ethylphenyl)ethyl)coformycin aglycone, mp 141° C.;

3-(2'-(3"-bromo-5"-carboethoxyphenyl)ethyl)coformycin aglycone, mp 132° C.;

3-(2'-(3"-carboethoxybiphen-5"-yl)ethyl)coformycin aglycone, mp 160° C.;

3-(2'-(3"-carbomethoxy-6"-methylphenyl)ethyl)coformycin aglycone, mp 199°–201° C.;

3-(2'-(3"-carboethoxy-6"-methylphenyl)ethyl)coformycin aglycone, mp 145°–150° C.;

3-(2'-(3"-carbobenzyloxy-6"-methylphenyl)ethyl) coformycin aglycone, mp 80°–85° C.;

3-(2-(3"-carboethoxy-6"-t-butyldimethylsilyloxy-methylphenyl) ethyl)coformycin aglycone as a deliquescent solid and standard treatment of this compound with TBAF provided 3-(2'-(3"-carboethoxy-6"-hydroxymethylphenyl)ethyl)coformycin aglycone as a deliquescent solid;

3-(2'-(3"-carbomethoxy-6"-ethylphenyl)ethyl)coformycin aglycone, mp 159° C.;

3-(2'-(3"-carbomethoxy-6"-propylphenyl)ethyl)coformycin aglycone, mp 164° C.;

3-(2'-(3"-carboethoxy-4"-methylphenyl)ethyl)coformycin aglycone, mp 155°–156° C.;

3-(2'-(3"-carbomethoxyphenyl)ethyl)coformycin aglycone, mp 143° C.;

3-(3'-(2"-methoxy-5"-carbomethoxyphenyl)propyl) coformycin aglycone, mp 164° C.;

3-(2'-(2"-methoxy-5"-carbomethoxyphenyl)ethyl) coformycin aglycone, mp 190°–195° C.;

3-(2'-(2"-fluoro-5"-carbomethoxyphenyl)ethyl coformycin aglycone, mp 203°–205° C.;

3-(2'-(3"-carbomethoxy-4"-fluorophenyl)ethyl coformycin aglycone, mp 179°–180° C.;

3-(2'-(3"-carbomethoxyphenoxy)ethyl)coformycin aglycone, mp 168°–170° C.;

3-(3'-(2"-carbomethoxyfuran-5"-yl)propyl)coformycin aglycone, mp 120°–122° C.;

3-(2'-carboethoxyfuran-5'-ylmethyl)coformycin aglycone, mp 130°–135° C.;

3-(2'-(2"-carbomethoxythiophen-4"-yl)ethyl)coformycin aglycone, mp 171° C.;

3-(3'-(2"-carbomethoxythiophen-3"-yl)propyl)coformycin aglycone, mp 187° C.;
3-(3'-(2"-carbomethoxy-3"-methyl-6"-isopropylphenyl) propyl)coformycin aglycone, mp 175°–180° C.;
3-(3'-(2"-carbomethoxy-6"-isopropylphenyl)propyl) coformycin aglycone, mp 168°–170° C.;
3-(5'-dimethyl phosphonyl)pentyl)coformycin aglycone, mp 80°–81° C.;
3-(6'-dimethyl phosphonyl)hexyl)coformycin aglycone, mp 93°–94° C.;
3-(5'-(dibenzyl phosphonyl)pentyl)coformycin aglycone, mp 81°–82° C.;
3-(6'-(dibenzyl phosphonyl)hexyl)coformycin aglycone, mp 71°–72° C.;
3-(2'-acetoxyethyl)coformycin aglycone, mp 164°–165° C.;
3-(3'-acetoxypropyl)coformycin aglycone, mp 103°–104° C.;
3-(4'-acetoxybutyl)coformycin aglycone, mp 134°–135° C.;
3-(5'-acetoxypentyl)coformycin aglycone, mp 93°–94° C.;
3-(6'-acetoxyhexyl)coformycin aglycone, mp 107°–108° C.;
3-(4'-cyanobutyl)coformycin aglycone, mp 146°–149° C.;
3-(6'-cyanohexyl)coformycin aglycone, mp 129°–132° C.;
3-ethylcoformycin aglycone, mp 189°–190° C.;
3-propylcoformycin aglycone, mp 159°–160° C.;
3-butylcoformycin aglycone, mp 163°–164° C.;
3-(3'-butenyl)coformycin aglycone, mp 151°–152° C.;
3-hexylcoformycin aglycone, mp 159°–160° C.;
3-heptylcoformycin aglycone, mp 152°–153° C.;
3-octylcoformycin aglycone, mp 151°–152° C.;
3-nonylcoformycin aglycone, mp 149°–150° C.;
3-(trans-3',7'-dimethyl-2',6'-octadienyl)coformycin aglycone, mp 156°–158° C.;
(3'R)-3-(3',7'-dimethyloct-6'-enyl)coformycin aglycone, mp 167°–168° C.;
(3'S)-3-(3',7'-dimethyloct-6'-enyl)coformycin aglycone, mp 164°–165° C.;
(3'S)-3-(3',7'-dimethyloctyl)coformycin aglycone, mp 170°–171° C.;
3-(4'-methyl-3'-pentenyl)coformycin aglycone, mp 160°–161° C.;
3-cyclohexylmethylcoformycin aglycone, mp 198°–199° C.;
3-cycloheptylmethylcoformycin aglycone, mp 199°–200° C.;
(1'S,2'S,5'S)-3-(6',6'-dimethyl[3.1.1]-bicyclohept-2'-methyl) coformycin aglycone, mp 207°–208° C.;
(1"R,2"S,5"R)-3-(2'-(2"-isopropyl-5"-methylcyclohexyloxy)-ethyl) coformycin aglycone, mp 168°–169° C.;
(1"S,2"R,5"S)-3-(2'-(2"-isopropyl-5"-methylcyclohexyloxy)-ethyl) coformycin aglycone, mp 168°–169° C.;
3-(2'-cyclohexylethyl)coformycin aglycone, mp 205°–206° C.;
3-(3'-cyclohexylpropyl)coformycin aglycone, mp 180°–181° C.;
3-(2'-cyclopentylethyl)coformycin aglycone, mp 205°–206° C.;
3-(naphth-2'-ylmethyl)coformycin aglycone, mp 190°–191° C.;
3-(2'-(naphth-2"-yl)ethyl)coformycin aglycone, mp 192°–193° C.;
3-(2'-phenylethyl)coformycin aglycone, mp 146°–147° C.;
3-(2'-(2"-methylphenyl)ethyl)coformycin aglycone, mp 180°–185° C.;
3-(3'-phenylpropyl)coformycin aglycone, mp 157°–158° C.;
3-(3'-(2",3",4",5"-tetrafluorophenyl)propyl)coformycin aglycone, mp 188°–189° C.;
3-(3'-phenyl-2'-propenyl)coformycin aglycone, mp 168°–169° C.;
3-(3'-(2"-methylphenyl)propyl)coformycin aglycone, mp 193°–195° C.;
3'-(2"-trifluoromethylphenyl)propyl)coformycin aglycone, 188°–192° C.;
3'-(3"-methylthiophen-2"-yl)propyl)coformycin aglycone, mp 185°–190° C.;
3-(3'-(2"-chlorophenyl)propyl)coformycin aglycone, mp 181°–182° C.;
3-(3'-3"-chlorophenyl)propyl)coformycin aglycone, mp 171°–172° C.;
3-(3'-4"-chlorophenyl)propyl)coformycin aglycone, mp 157°–158° C.;
3-(3'-2"-bromophenyl)propyl)coformycin aglycone, mp 186°–187° C.;
3-(3'-3"-bromophenyl)propyl)coformycin aglycone, mp 165°–166° C.;
3-(3'-4"-bromophenyl)propyl)coformycin aglycone, mp 147°–148° C.;
3-(3'-2"-ethoxyphenyl)propyl)coformycin aglycone, mp 168°–169° C.;
3-(3'-3"-ethoxyphenyl)propyl)coformycin aglycone, mp 136°–137° C.;
3-(3'-4"-ethoxyphenyl)propyl)coformycin aglycone, mp 117°–118° C.;
3-(3'-2"-benzyloxyphenyl)propyl)coformycin aglycone, mp 129°–130° C.;
3-(3'-(3"-benzyloxyphenyl)propyl)coformycin aglycone, mp 123°–124° C.;
3-(3'-(4"-benzyloxyphenyl)propyl)coformycin aglycone, mp 154°–155° C.;
3-(3'-(4"-methoxyphenyl)propyl)coformycin aglycone, mp 165°–166° C.;
3-(3'-(4"-trifluoromethoxyphenyl)propyl coformycin aglycone, mp 123°–124° C.;
3-(3'-(4"-propoxyphenyl)propyl)coformycin aglycone, mp 134°–135° C.;
3-(3'-(4"-butoxyphenyl)propyl)coformycin aglycone, mp 135°–136° C.;
3-(3'-(4"-isopropylphenyl)propyl)coformycin aglycone, mp 161°–162° C.;
3-(3'-(4"-propylphenyl)propyl)coformycin aglycone, mp 139°–140° C.;
3-(3'-(biphenyl-4"-yl)propyl)coformycin aglycone, mp 174°–175° C.;
3-(3'-(2", 4"-dimethylphenyl)propyl)coformycin aglycone, mp 167° C.;
3-(3'-(2", 5"-dimethylphenyl)propyl)coformycin aglycone, mp 174° C.;
3-(3'-(2", 4", 6"-trimethylphenyl)propyl)coformycin aglycone, mp 181° C.;
3-(2'-phenylbutyl)coformycin aglycone, mp 161°–162° C.; and
3-(6'-(2"-bromophenyl)hexyl)coformycin aglycone, mp 136°–137° C.;

Example 34

Preparation of 3-(3'-(Hydroxyphenyl)propyl)coformycin Aglycones.

The 3-(3'-(benzyloxyphenyl)propyl)coformycin aglycone was hydrogenated using previously described conditions to provide the title compound.

The following compounds were prepared in this manner:
3-(3'-(2"-hydroxyphenyl)propyl)coformycin aglycone, mp 140°–141° C.;
3-(3'-(3"-hydroxyphenyl)propyl)coformycin aglycone, mp 144°–145° C.; and 3-(3'-(4"-hydroxyphenyl)propyl)coformycin aglycone, mp 123°–124 °C.

Example 35
Preparation of 5-Methyl-3-(3'-(2"-methylphenyl)propyl)-coformycin aglycone.

The compound 6,7-dihydro-5-methylimidazo[4,5-d][1,3]diazepin-8(3H)-one was alkylated and reduced by a previously described method to provide the title compound: mp 82° C.

Example 36
Preparation of 3-(3'-(2"-Methylphenyl)propyl)-4,5,6,8-tetrahydro-7H-imidazo[4,5-d][1,3]diazepine-5-one-8-ol.

The compound 4,5,6,8-tetrahydro-1H,7H-imidazo[4,5-d][1,3]diazepine-5,8-dione (prepared by the method of Hosmane, et al., Nucleosides & Nucleotides 1991, 10, 1693–1706) was alkylated and reduced by a previously described method to provide the title compound: mp 218° C.

Example 37
Preparation of 7-Methyl-3-(3'-phenylpropyl)coformycin aglycones.

The compound 6,7-dihydro-7-methylimidazo[4,5-d][1,3]diazepin-8(3H)-one was alkylated and reduced by a previously described method to provide a mixture of the title compounds: mp 89°–90° C.

Example 38
Preparation of 3-Cycloheptyl Coformycin Aglycone.

A mixture of 1 mmol 6,7-Dihydroimidazo[4,5-d][1,3]diazepin-8(3H)-one (1.3 mmol), 1 mmol cycloheptylbromide and 2 mmol $Cs_2CO_3$ in 5 mL of DMF was stirred for 4 h at 75° C. Chromatography provided 3-cycloheptyl-8-ketocoformycin aglycone which ws reduced with sodium borohydride as previously described to produce the title compound: mp 187°–189° C.

Example 39
Preparation of 3-Substituted 6-Acetylcoformycin Aglycones.

A mixture of 1 mmol of a 3-substituted coformycin aglycone and 3 mmol of thioacetic acid in 10 mL of DMF was stirred at rt for 16 h. Chromatography provided the title compound.

The following compounds were prepared in this manner:
3-heptyl-6-acetylcoformycin aglycone, mp 138°–141° C.; and
3-(3'-phenylpropyl)-6-acetylcoformycin aglycone as a deliquescent solid.

Example 40
Preparation of 3-substituted-8-heterosubstituted-3,6,7,8-tetrahydroimidazo[4,5-d][1,3]diazepine.

A mixture of 1 mmol of the 3-substituted 6-acetylcoformycin aglycone, 3 mmol of DEAD, 3 mmol of $PPh_3$ and 3 mmol of thioacetic acid or diphenylphosphorylazide in 10 mL of THF was stirred at 0° C. for 6 h. Chromatography provided the 8-substituted compound which after stirring in methanolic ammonia for 30 min at 0° C. and evaporating the solvent provided the title compounds.

The following compounds were prepared in this manner:
3-heptyl-8-mercapto-3,6,7,8-tetrahydroimidazo[4,5-d][1,3]diazepine as an oil,
3-(3'-propylphenyl)-8-azido-3,6,7,8-tetrahydroimidazo[4,5-d][1,3]diazepine as an oil and
3-(3'-propylphenyl)-8-amino-3,6,7,8-tetrahydroimidazo[4,5-d][1,3]diazepine as an oil from hydrogenation of the 8-azido analog under previously described conditions.

Example 41
Preparation of 3-Heptyl-8-methylcoformycin Aglycone.

A mixture of 1 mmol of 3-heptyl-8-ketocoformycin aglycone and 1.1 mmol of NaH in 5 mL of DMF was stirred for 30 min and then 1.1 mmol of trimethylsilylethoxymethyl chloride SEM-Cl) was added and after stirring for 6 h, extraction and chromatography provided the 6-SEM substituted derivative.

To a solution of 1 mmol of this compound in 10 mL of THF at −78° C. was added 3 mmol of etheral MeLi and after 1 h, extraction and chromatography provided 3-heptyl-6-SEMyl-8-methylcoformycin aglycone.

A mixture of 1 mmol of this compound and 1.5 mmol of TBAF in 10 mL of DMF was stirred at 80° C. for 3 h and then chromatography provided the title compound: mp 133°–136° C.

Example 42
General Procedure for Ester Hydrolysis to a Sodium Carboxylate.

The ester (1 mm) was stirred at rt in 13 mL of 0.1N sodium hydroxide for 2 h and then the pH lowered to 7 by the addition of Amberlite CG-50 resin. The solution was filtered over Celite and lyophilized to provide the carboxylate sodium salt.

The following compounds were prepared in this manner:
3-(5-carboxypentyl)coformycin aglycone sodium salt, mp 250° C. (dec);
3-(6'-carboxyhexyl)coformycin aglycone, mp 165°–168° C.;
3-(7'-carboxyheptyl)coformycin aglycone, mp 166°–166° C.;
3-(3'-carboxypropoxymethyl)coformycin aglycone sodium salt as a deliquescent solid;
3-(5'-carbobenzyloxy-5'-carboxyhexyl)coformycin aglycone sodium salt, and in this case, dioxane in a volume equivalent to that of sodium hydroxide was added to provide the title compound, mp 62°–65° C.;
3-(2'-(2"-carboxycyclopropyl)ethyl)coformycin aglycone sodium salt as a deliquescent solid,
3-(2'-(o-carboxyphenoxy)ethyl)coformycin aglycone sodium salt as a deliquescent solid,
3-(p-carboxyphenylethyl)coformycin aglycone sodium salt as a deliquescent solid,
3-(p-carboxymethylbenzyl)coformycin aglycone sodium salt as a deliquescent solid,
3-(2'-(o-carboxyphenylthio)ethyl)coformycin aglycone sodium salt as a deliquescent solid,
3-(2'-(m-carboxyphenoxy)ethyl)coformycin aglycone sodium salt as a deliquescent solid,
3-(3'-(3"-carboxy-6"-methylphenyl)propyl)coformycin aglycone sodium salt as a deliquescent solid,
3-(3'-(o-carboxyphenyl)propyl)coformycin aglycone sodium salt as a deliquescent solid,
3-(3'-(m-carboxyphenyl)propyl)coformycin aglycone sodium salt as a deliquescent solid and
3-(3'-(mercaptoacetoxy)propyl)coformycin aglycone sodium salt as a deliquescent solid.

Example 43
General Procedure for Ester Hydrolysis to a Carboxylic Acid.

One mmol of the ester was stirred at rt in 13 mL of 0.1N sodium hydroxide for 2 h and then the solution was subjected to ion exchange chromatography on Dowex-1-acetate eluting first with water and then with 0.1N acetic acid to provide the desired carboxylic acid.

The following compounds were prepared in this manner:
3-(5'-carboxy-6'-phenylhexyl)coformycin aglycone, prepared as described only an equal volume of dioxane was added and the mixture was heated for 16 h at 60° C. to effect hydrolysis, mp 3-(5'-carboxy-6'-(2"-bromophenyl)hexyl)coformycin aglycone, mp 111° C.;

3-(5'-carboxy-6'-3"-bromophenyl)hexyl)coformycin aglycone, mp 98° C.;

3-(5'-carboxy-6'-4"-bromophenyl)hexyl)coformycin aglycone, mp 116° C.;

N-(3-(3',6',7',8'-tetrahydroimidazo[4',5'-d]-[1',3']diazepin-8'-ol-3'-yl)propyl)-N-formyl-D-phenylalanine, 118°–122° C.;

3-(5',5'-dicarboxypentyl)coformycin aglycone, prepared as described from 3-(5',5',5'-tricarbobenzyloxypentyl) coformycin aglycone only an equal volume of dioxane and 2 mmol of NaOH were added and the product was isolated by ion exchange chromatography and preparative reverse phase chromatography, mp 85°–90° C.;

3-(5'-carboxy-5'-carbobenzyloxypentyl)coformycin aglycone, prepared as described from 3-(5',5',5'-tricarbobenzyloxypentyl)coformycin aglycone only an equal volume of dioxane and 2 mmol of NaOH were added and the product was isolated by ion exchange chromatography and preparative reverse phase chromatography, mp 53°–58° C.

3-(3'-(2'-carboxy-5"-methylphenyl)propyl)coformycin aglycone, mp 122°–125° C.;

3-(3'-carboxyphenylmethyl)coformycin aglycone, mp 205°–207° C.;

3-(3'-(2'-carboxyfuran-5'-yl)propyl)coformycin aglycone, 190° C. (dec);

3-(2'-carboxyfuran-5'-ylmethyl)coformycin aglycone, mp 240° C. (dec);

3-(3'-(2"-carboxy-6"-isopropylphenyl)propyl)coformycin aglycone, mp 210° C. (dec);

3-(3'-(2'-methoxy-5"-carboxyphenyl)propyl)coformycin aglycone, mp 225° C.;

3-(3'-(2'-fluoro-5"-carboxyphenyl)ethyl)coformycin aglycone, mp 230°–240° C.;

3-(2'-(2"-methoxy-5"-carboxyphenyl)ethyl)coformycin aglycone, mp 180°–190° C. (dec);

3-(2'-(3"-carboxy-4"-methylphenyl)ethyl)coformycin aglycone as a deliquescent solid;

3-(2'-(3"-carboxy-4"-fluorophenyl)ethyl)coformycin aglycone, mp 220°–230° C. (dec);

3-(2'-(3"-carboxy-5"-ethylphenyl)ethyl)coformycin aglycone, mp 130° C. (dec);

3-(2'-(3"-carboxybiphen-5"-yl)ethyl)coformycin aglycone, mp 220° C. (dec);

3-(2'-(3"-bromo-5"-carboxyphenyl)ethyl)coformycin aglycone, mp 226° C.;

3-(2'-(3"-carboxy-6"-methylphenyl)ethyl)coformycin aglycone, mp 140°–150° C.;

3-(2'-(3"-carboxy-6"-ethylphenyl)ethyl)coformycin aglycone, mp 215° C.;

3-(2'-(3"-carboxy-6"-propylphenyl)ethyl)coformycin aglycone, mp 250° C.;

3-(2'-(3"-carboxy-6"-hydroxymethylphenyl)ethyl) coformycin aglycone, mp 140°–150° C.;

3-(2'-(3"-carboxyphenyl)ethyl)coformycin aglycone, mp 210° C.;

3-(3'-(2"-carboxy-3"-fluorophenyl)propyl)coformycin aglycone, mp 205° C.;

3-(3'-(2"-carboxy-4"-methylphenyl)propyl)coformycin aglycone, mp 204° C.;

3-(3'-carboxymethylbenzyl)coformycin aglycone, mp 207° C.;

3-(3'-(2"-carboxynaphthyl)propyl)coformycin aglycone, mp 200°–210° C.;

3-(2'-(3"-carboxynaphthyl)ethyl)coformycin aglycone, mp 190°–235° C. (dec);

3-(3'-(2"-carboxythiophen-3"-yl)propyl)coformycin aglycone, mp 210° C. (dec);

3-(2'-(2"-carboxythiophen-4"-yl)ethyl)coformycin aglycone, mp 230° C. (dec);

3-(2'-(2"-carboxythiophen-5"-yl)ethyl)coformycin aglycone as a deliquescent solid and 3-carboxyethylthioethylcoformycin aglycone, mp 106° C.

Example 44

Preparation of N-(4-(3', 6',7', 8'-Tetrahydroimidazo-[4', 5'-d]-[1',3']diazepin-8'-ol-3'-yl)butyryl)glycine Dicyclohexyl Ammonium Salt. General Procedure for the Synthesis of Amino Acid Adducts.

A mixture of 1 mmol of 3-(3'-carbobenzyloxypropyl) coformycin aglycone and 10 mg of 10% Pd/C in 4 mL of methanol was subjected to hydrogenation. After filtration and removal of the solvent, 3-(3'-carboxypropyl)coformycin aglycone was obtained. This product, 2 mmol glycine ethyl ester hydrochloride, 2 mmol triethylamine, 2 mmol dicyclohexylcarbodiimide and 2 mmol N-hydroxysuccinimide in 10 mL DMF were stirred 16 h and filtered. Chromatography provided N-(4-(3,6,7,8-tetrahydro-imidazo[4,5-d]-[1,3] diazepin-8-ol-3-yl)butyryl)glycine ethyl ester.

This ester was hydrolyzed as previously described to provide N-(4-(3,6,7,8-tetrahydroimidazo[4,5-d]-[1,3] diazepin-8-ol-3-yl)butyryl)glycine. To a solution of this acid in methanol was added dicyclohexylamine and then the solvent evaporated and the residue triturated with acetone to provide the title compound: mp 222° C.

The following compounds were prepared in this manner:

N-(4-(3',6',7',8'-tetrahydroimidazo[a',5'-d]-[1',3']diazepin-8'-ol-3'-yl)butyryl)-L-phenylalanine dicyclohexyl ammonium Salt, mp 220° C.;

N-(4-(3',6',7',8'-tetrahydroimidazo-[4',5'-d]-[1',3']diazepin-8'-ol-3'-yl)butyryl)-D-phenylalanine dicyclohexyl ammonium salt, mp 162°–165° C.; and N-(4-(3',6',7',8'-tetrahydroimidazo-[4',5'-d]-[1',3']diazepin-8'-ol-3'-yl)butyryl)-L-valine Dicyclohexyl Ammonium Salt, mp 223° C.

Example 45

Preparation Of 3-(5'-Carbox-N-substituted-amido-5'-carboxyhexyl)coformycin Aglycones.

A mixture of 1 mmol of 3-(5'-carbobenzyloxy-5'-carboxyhexyl)coformycin aglycone, 1.5 mmol of an amine, 1.5 mmol of diphenylphosphorylazide and 3 mmol of triethylamine in 10 mL of DMF were stirred at 16 h at ft. Chromatography provided the ester-amide compound which was subjected to ester hydrolysis by the previously described method to provide the title compound.

The following compounds were prepared in this manner:

3-(5'-carbox-N-benzylamido-5'-carboxyhexyl)coformycin aglycone, mp 175° C.;

3-(5'-carbox-N-(4"-chlorobenzyl)amido-5'-carboxyhexyl) coformycin aglycone, mp 111° C.;

3-(5'-carbox-N-(2"-phenethyl)amido-5'-carboxyhexyl) coformycin aglycone, mp 93° C.;

3-(5'-carbox-N-cyclohexylamido-5'-carboxyhexyl) coformycin aglycone, mp 199°–203° C.; and 3-(5'-carbox-N-cyclohexylmethylamido-5'-carboxyhexyl) coformycin aglycone, mp 116° C.

Example 46

Preparation of 3-(5'-Carboxamido-5'-carboxyhexyl) coformycin Aglycone.

The compound 3-(5'-carbox-N-phenylamido-5'-carbobenzyloxyhexyl)coformycin aglycone, prepared as above was subjected to hydrogenation by the previously described method to provide the title compound: mp 170° C.

Example 47
Preparation of 3-(5'-(Tetrazol-5"-yl)pentyl)coformycin aglycone dicyclohexylammonium salt.

6,7-Dihydroimidazo[4,5-d][1,3]diazepin-8(3H)-one and 5-(5'-bromopentyl)-2-trimethylsilylethoxymethyltetrazole were subjected to the general alkylation and reduction sequence to provide 3-(5'-((2"-trimethylsilylethoxy-methyl) tetrazol-5"-yl)pentyl)coformycin aglycone as a deliquescent solid.

A mixture of 1 mmol of this compound and 1.5 mmol of TBAF in 10 mL of DMF were stirred at 50° C. for 2 h. The mixture was evaporated and the residue dissolved in 5 mL of water and subjected to ion-exchange chromatography on Dowex-1-acetate eluting with water and then 0.05M AcOH to give the tetrazole. It was dissolved in methanol and dicyclohexylamine was added. Evaporation and trituration with acetone provided the title compound: mp 220° C.

The following compound was also prepared in this manner:

3-(2'-(6"-methyl-3-(tetrazol-5'H-yl)phenyl)ethyl) coformycin aglycone: mp 190° C. (dec).

Example 48
Preparation of 3-(6'-(Methyl phosphonoxy)hexyl) coformycin Aglycone.

A solution of 1 mmol of 3-[6'-(dimethyl phosphonyl) hexyl]coformycin aglycone and 20 mmol lithium methoxide in 10 mL of methanol was stirred for 72 h at 50° C. The mixture was cooled and methanolic HCl was added to pH to 1. Reverse phase chromatography provided the title compound: mp 67°–68° C.

Example 49
Preparation of 3-(5'-Phosphonoxypentyl)coformycin Aglycone.

A suspension of 1 mmol of 3-[5'-(dibenzyl phosphonyl) pentyl]coformycin aglycone and 50 mg of 10% Pd/C in 10 mL of 1:1 water-methanol was hydrogenated. The mixture was filtered through Celite, concentrated and lyophilized to provide the title compound: mp 119°–120° C.

The following compounds were prepared in this manner:
3-(6'-phosphonoxyhexyl)coformycin aglycone, mp 210° C. (dec);

and 3-(5',5'-dicarboxyhexyl)coformycin aglycone dicyclohexyl ammonium salt, prepared in the same manner only dicyclohexylammine was included during hydrogenation, mp 155° C. (dec).

Example 50
General Procedure for Acetate Methanolysis to a 3-(Hydroxyalkyl)coformycin Aglycone.

A solution of 1 mmol of 3-(acetoxyalkyl)coformycin aglycone and 5 mL of a 0.5M solution of sodium methoxide in methanol was stirred for 0.5 hours. Amberlite CG-50 resin was added until pH 7. Filtration throough celite, solvent removal and crystallization from ether-methanol provided the title compound.

The following compounds were prepared in this manner:
3-(2'-hydroxyethyl)coformycin aglycone, mp 220°–221° C.;
3-(3'-hydroxypropyl)coformycin aglycone, mp 210°–211° C.;
3-(4'-hydroxybutyl)coformycin aglycone, mp 176°–177° C.;
3-(5'-hydroxypentyl)coformycin aglycone, mp 135°–136° C.; and
3-(6'-hydroxyhexyl)coformycin aglycone, mp 138°–139° C.

Example 51
Preparation of 3-(5'-Carboxamidopentyl)coformycin Aglycone.

A solution of 3-(5'-carboethoxypentyl)coformycin aglycone in 4 mL of a 15% $NH_3$ in methanol solution was heated in a sealed reaction vessel at 100° C. for 72 h. Then the solvent was removed and the residue recrystallized from ether-methanol to provide the title compound: mp 159°–163° C. dec).

For the purposes of clarity and brevity, chemical compounds are referred to as numbers in the biological examples below. The following is a list of the chemical names associated with the compound numbers:

3-heptylcoformycin aglycone (compound 1a),
3-heptyl-8-methylcoformycin aglycone (compound 1b),
(3'S)-3-(3',7'-dimethyloct-6'-enyl)coformycin aglycone (compound 1c),
3-cycloheptylcoformycin aglycone (compound 1d),
(1'S,2'S,5'S)-3-(6',6'-dimethyl[3,1,1]-bicyclohept-2'-methyl) coformycin aglycone (compound 1e),
3-(3'-(2"-methylphenyl)propyl)coformycin aglycone (compound 1f),
5-methyl-3-(3'-(2"-methylphenyl)propyl)coformycin aglycone (compound 1g),
3-(3'-propylphenyl)-8-azido-3,6,7,8-tetrahydroimidazo[4,5-d][1 3]diazepine (compound 1h),
3-(3'-(4"-propoxyphenyl)propyl)coformycin aglycone (compound 1i),
3-(5'-carboxy-6'-phenylhexyl)coformycin aglycone (compound 1j),
3-(5'-carboxy-5'-carbobenzyloxypentyl)coformycin aglycone (compound 1k),
3-(5'-carbox-N-benzylamido-5'-carboxyhexyl)coformycin aglycone (compound 1l),
3-(2'-(3"-carboxy-6"-methylphenyl)ethyl)coformycin aglycone (compound 1m),
3-(2'-(6"-methyl-3"-(tetrazol-5'"-yl)phenyl)ethyl) coformycin aglycone (compound 1n),
3-(2'-(2"-carboxythiophen-4"-yl)ethyl)coformycin aglycone (compound 1o),
3-(2'-(3"-carboxynaphthyl)ethyl)coformycin aglycone (compound 1p),
3-(2'-(3"-bromo-5"-carboxyphenyl)ethyl)coformycin aglycone (compound 1q) and
3-(5'-carboxy-6'-(3"-bromophenyl)hexyl)coformycin aglycone (compound 1r).

Example A
AMP Deaminase Assay

Inhibition of AMPDA activity from porcine heart was determined at 37° C. in a 0.1 ml assay mixture containing inhibitor, ~0.005 U AMPDA, 0.1% bovine serum albumin, 10 mM ATP, 250 mM KCl, and 50 mM MOPS at pH 6.5. The concentration of the substrate AMP was varied from 0.125-10.0 mM. Catalysis was initiated by the addition of enzyme to the otherwise complete reaction mixture, and terminated after 5 minutes by injection into an HPLC system. Activities were determined from the amount of IMP formed during 5 minutes. IMP was separated from AMP by HPLC using a Beckman Ultrasil-SAX anion exchange column (4.6 mm×25 cm)with an isocratic buffer system (12.5 mM potassium phosphate, 30 mM KCl, pH 3.5) and detected spectrophotometrically by absorbance at 254 nm. Values of the inhibition constant Ki were calculated from the dependence of activity on substrate and inhibitor concentrations assuming competitive inhibition:

$$v = V_{max}[AMP]/\{[AMP] + K_m(1 + [I]/K_i)\}$$

where v is the measured catalytic rate, Vmax is the maximal rate at saturating concentrations of AMP and in the absence of inhibitor I, and Km is the Michaelis constant for AMP.

For ease of comparison, data obtained by this assay is presented in the table of example B.

Example B
Adenosine Deaminase Assay

Inhibition of adenosine deaminase (ADA) from calf intestinal mucosa was determined spectrophotometrically at pH 7.0 using one of the following two assays:

(1) Direct Assay: The reaction system mixture contained inhibitor, ~0.001 units ADA, and 40 mM potassium phosphate in 1 ml and at 37° C. The concentration of the substrate adenosine was varied from 20 to 100 µM. The reaction was initiated by addition of ADA and monitored continuously at 265 nm for 15 minutes as the decrease in absorbance reflects conversion of adenosine to inosine.

(2) Coupled Assay Based Upon the Following Reaction Scheme:

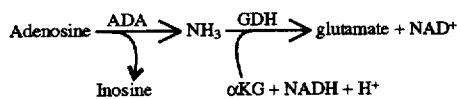

The reaction mixture contained 100 µM adenosine, ~0.001 U ADA, 2.5 mM a-ketoglutarate (aKG), 250 µM NADH, 400 µM ADP, ~10 U glutamate dehydrogenase (GDH), and 50 mM potassium phosphate in 0.2 ml and at room temperature. The reaction was initiated by addition of adenosine and monitored continuously at 340 nm for 7 minutes as the decrease in absorbance reflects oxidation of NADH.

The following table gives the inhibition constants for AMPDA and ADA of representative compounds of the present invention. The selectivity ratio was determined as: selectivity ratio=[ADA Ki/Km]/[AMPDA Ki/Km].

| Compound | AMPDA Ki* | ADA Ki* | Selectivity Ratio** |
|---|---|---|---|
| 1a | 10 | 0.35 | 0.60 |
| 1b | 36 | 12 | 6 |
| 1c | 1.1 | 1.9 | 29 |
| 1d | 8.0 | 7.9 | 17 |
| 1e | 1.7 | >160 | >1.6K |
| 1f | 2.1 | 0.042 | 0.34 |
| 1g | 11 | >100 | >150 |
| 1h | 6.6 | 0.063 | 0.16 |
| 1i | 3.6 | 0.006 | 0.03 |
| 1j | 0.41 | >200 | >8.3K |
| 1k | 0.36 | >1K | >47K |
| 1l | 2.7 | >1K | >6.3K |
| 1m | 0.097 | >1K | >175K |
| 1n | 1.6 | >200 | >2.1K |
| 1o | 2.2 | >6 | 590 |
| 1p | 0.020 | >1K | >850K |

\* = values are in µM
\*\* K = 1,000

Example C
Inhibition of Neutrophil-Myocyte Adhesion

Isolated neutrophils and myocytes were stimulated with the cytokine, TNF-α, and incubated in the presence of the test compound. Neutrophil-myocyte adhesion was determined as described by Entman, et al., *J. Clin. Invest.* 85:1497–1506 (1990). The following table gives $IC_{50}$ values obtained for representative compounds of the present invention. This inhibition was completely reversed in the presence of adenosine deaminase (ADA), demonstrating inhibition was mediated by increased adenosine levels.

| Neutrophil-Myocyte Adhesion Inhibition | |
|---|---|
| Compound | $IC_{50}$ (µM) |
| 1a | 12 ± 6 |
| 1c | 5.1 ± 2.5 |
| 1d | 4.3 ± 1.3 |
| 1e | 24 ± 3 |
| 1f | 1.4 ± 0.45 |
| 1j | 0.045 ± 0.01 |
| 1m | 0.030 ± 0.01 |
| 1o | 8.0 ± 2 |

Example D
Improved Functional Recovery in Ischemic Hearts

The ability of AMP deaminase inhibitors of the present invention to improve the recovery of post-ischemic function was examined in an isolated rat heart model of ischemia-reperfusion injury.

Isolated rat hearts were cannulated via the ascending aorta and attached to a perfusion apparatus according to the method of Langendorff. The hearts were perfused at a constant pressure of 100 cm of $H_2O$ with a modified Krebs-Hanseleit buffer (pH 7.4) at 37° C. Left ventricular developed pressures (LVDP) were monitored continuously using a latex balloon attached to a pressure transducer. Coronary flows were measured gravimetrically by timed collection of pulmonary effluent. Following equilibration of the hearts for a period of 30 minutes, the hearts were subjected to 430 minutes of low flow ischemia, by reducing the perfusion pressure to 10 cm of $H_2O$, and then reperfused for 30 minutes by restoring the pressure to its original level (100 cm of $H_2O$). Two compounds of the present invention, compound 1a and compound 1m, were tested in this assay. Compound 1a provided recovery of LVDP to 83±3% compared to the placebo value of 69±1% when added to the perfusion to give a concentration of 3 µM. Compound 1 m provided recovery of LVDP to 83±2% compared to the placebo value of 65±2% when added to the perfusion to give a concentration of 0.3 µM.

Example E
Inhibition of Seizures

The following compounds of the present invention were examined for ability to inhibit electrically-induced seizures in rats: compound 1d, compound 1e, compound if and compound 1c.

Maximal electroshock (MES)seizures were induced in male Sprague Dawley rats by administering a 150 mA, 60-Hz sinewave current for 0.2 sec via corneal electrodes. The MES stimulus was presented 30 min following intraperitoneal injection of the test compound. The endpoint measured was percentage of animals in which hind limb tonic extension (HTE) was suppressed; suppression level is 0% in vehicle-treated animals. All of the test compounds elicited 25-67% (n=6 per compound) suppression at a dose of 10–30 mg/kg. These results indicate that AMPDA inhibitors inhibit MES seizures in rats.

Example F
Effect of AMPDA Inhibitor In A Rat Model Of Ischemic Brain Injury

Each rat is anesthetized with halothane and placed on a heating pad hooked up to a temperature regulator and connected to rectal probe. EEG electrodes are then inserted into the temporalis muscle bilaterally in between the eye and the ear. A midline incision is made to expose the left Common Carotid Artery (CCA). The internal Carotid Artery (ICA) is isolated and carefully separated from the adjacent vagus nerve. Following ligation of various vessels the ICA should be the only remaining extracranial branch of the CCA. Two 5-0 silk sutures are tied loosely around the external carotid artery (ECA) and microvascular clips placed on both the CCA (proximal to the bifurcation) and the ICA (in between the first and the second bifurcation). The ECA above the bifurcation is coagulated and the two sutures are then cut below the coagulation. A 25 mm length 4–0 nylon suture, its tip rounded by heating near a fine tipped cauterizer, is introduced into the ECA lumen. 20–22 mm of the suture is inserted into the ECA stump. The suture around the ECA is tightened to hold the occluding suture in place and EEC reading is checked to confirm occlusion by the appearance of a flat line. At this point the intraluminal suture has blocked the origin of the Middle Carotid Artery (MCA), occluding all sources of blood flow from the interior Carotid Artery (ICA), the anterior Carotid Artery (ACA), and the posterior cerebral artery (PCA). At 105 min later the suture is gently retracted under halothane anesthesia to allow blood flow back into the middle cerebral artery. The neck incision is closed and animals allowed to recover from anesthesia. At 24 hrs animals are evaluated for behavioral deficits, sacrificed, transcardial perfused, brains removed and TTC stained for visualization of infarcted region using a computer assisted system.

The application of compound 1d is shown in the time line diagram. Thirty minutes prior to induction of ischemia (SUTURE IN) Compound 1d in isotonic saline solution was infused for 15 min at a loading dose of 250 µg/kg/min (50 µl/min) followed by maintenance rate of 50 µg/kg/min for the remaining 12 hrs.

As shown below, infusion of compound 1d had no apparent effect on a number of physiological parameters such as blood pressure, heart rate, body temperature and blood gases. Infusion of Compound 1d did have a significant effect on infarct volume in this model of focal ischemia in the rat. Drug infusion reduced infarct volume by 52% from 139±31 (n=7) to 71±28 (n=8) mm$^3$ (p=0.05).

Effect of Continuous Infusion with Compound 1d on Various Parameters in the Rat Focal Stroke Model

| Parameter | Control* | Treated* | p Value |
|---|---|---|---|
| pH | 7.398 ± 0.012 | 7.379 ± 0.015 | 0.36 |
| pCO$_2$ | 36.1 ± 1.1 | 37.8 ± 1.3 | 0.36 |
| pO$_2$ | 144.6 ± 2.1 | 142.3 ± 10.0 | 0.86 |
| Temperature** | | | |
| T = 0 | 37.8 ± 0.2 | 37.4 ± 0.2 | 0.15 |
| T = 60 | 37.5 ± 0.1 | 37.5 ± 0.2 | 0.7 |
| Post reperfusion | 38.6 ± 0.2 | 38.6 ± 0.2 | 0.98 |
| Blood Pressure‡ | | | |
| Pre | 102 ± 4 | 102 ± 5 | 0.99 |
| T = 60 | 89 ± 9 | 84 ± 9 | 0.72 |
| Post reperfusion | 117 ± 5 | 115 ± 4 | 0.67 |

\* = mean ± sem
\*\* = in °C.
‡ = in mm Hg

We claim:
1. A compound of the formula

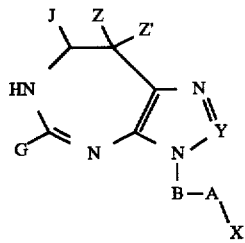

wherein
Y is —C(K)—;
K is hydrogen, halogen, azido, or amino;
G is hydrogen, lower alkyl, or amino;
Z is azido, hydroxy, thio, lower acyloxy, or lower thioacyloxy;
Z' is hydrogen or lower alkyl;
J is hydrogen or lower alkyl;
B is a straight or branched divalent group selected from lower alkylene, lower alkylenylaryl, lower alkylenylamino, lower alkylenylaminoalkylene, lower alkylenylaminoaryl, lower alkylenyloxyaryl, lower alkylenylacylamino, lower alkylenyloxyalkyenylaryl, lower alkylenylacylaminoalkylene, lower alkyleneoxy, lower alkoxyalkyl, lower alkylenethio, lower alkylthioalkyl, lower alkynyl, lower alkenyl, alkylcarboxamidoalkyl, alkylcarboxamidoalkylaryl, hydroxylated lower alkylene, halogenated lower alkylene, halogenated lower alkylenylaryl, alkylenetetrazolo, alkylene-3H-1,2,3,5-oxythiodiazolo, alkylenethiazolidine-2,4-diono, alkyleneoxazolidin-2,4-diono or is a direct link;
A is a divalent group selected from a straight or branched alicyclic group, a straight or branched heteroalicyclic group, aryl group or heteroaryl group, all optionally substituted with substituents independently selected from lower alkyl, lower aryl, lower aryloxy, aralkyl, perhaloalkoxy, aralkoxy, heteroaryl, heteroaryloxy, heteroarylalkyl, heteroaralkoxy, azido, amino, guanidino, halogen, hydroxy, lower alkoxy, lower alkylthio, carboxyalkyl, carboxyl, carboxamido, carboxamidoalkylaryl, carboxamidoaryl, aminocarboxamidoalkyl, cyano, lower perhaloalkyl, or is a direct link;
X is hydrogen, lower alkyl, lower alkoxy, halogen, hydroxy, acyloxy, thio, amino, azido, cyano, carboxyl, carboxyalkyl, carboxyaryl, carboxyaralkyl, tetrazolo, 3H-1,2,3,5-oxythiodiazolo, thiazolidine-2,4-diono, oxazolidin-2,4-diono, carboxamido, carboxamidoalkyl, carboxamidoaralkyl, carboxamidoaryl, guanidino, —PO$_3$EE', or C(W)CO$_2$E (COQ);
E and E' are independently selected from hydrogen, lower alkyl, aryl or aralkyl;
W is hydrogen, lower alkyl, halogenated lower alkyl, carboxyalkyl, carboxyaralkyl, or halogen;
Q is lower alkyl, lower alkoxy, aralkoxy, lower alkylthio, alkylamino, hydroxy, amino, arylamino, aralkylamino or aryloxy;
and pharmaceutically acceptable salts thereof;
with the proviso that (a) when B is a direct link, then A is not substituted tetrahydrofuran or substituted cyclopentylene;

(b) when B is lower alkoxyalkyl and A is a direct link, then X is not hydroxy;

(c) when B is methylene and A is a direct link, then X is not hydrogen;

(d) when B is methylene, X is hydrogen then A is not phenyl; and (e) A and B cannot both be direct links.

2. A compound of claim 1 where K is hydrogen.

3. A compound of claim 1 where G is hydrogen or methyl.

4. A compound of claim 1 where Z is hydroxy or azido and Z' is hydrogen.

5. A compound of claim 1 where Z is hydroxy and Z' is lower alkyl of one to three carbons.

6. A compound of claim 1 where J is hydrogen.

7. A compound of claim 1 where B is straight or branched lower alkylene, lower alkylenylaryl or a direct link.

8. A compound of claim 1 where A is a divalent group selected from a straight or branched alicyclic group, a straight or branched heteroalicyclic group, aryl or heteroaryl, all optionally substituted with substituents independently selected from amino, halogen, hydroxy, cyano, lower alkyl, lower alkoxy, lower aryl, lower aryloxy, aralkyl, aralkoxy, heteroaryl or is a direct link.

9. A compound of claim 1 where X is hydrogen, carboxyl, carboxyalkyl, carboxyaryl, carboxyaralkyl, tetrazolo, 3H-1,2,3,5-oxythiodiazolo, thiazolidine-2-,4-diono, oxazolidin-2,4-diono, or C(W)CO$_2$E(COQ);

where m and E' are independently selected from hydrogen, lower alkyl, aryl or aralkyl;

W is hydrogen or lower alkyl;

Q is lower alkoxy, aralkoxy, aralkylamino, alkylamino, hydroxy, amino, arylamino or aryloxy.

10. A compound of claim 2 where Z is hydroxy or azido and Z' is hydrogen and the carbon to which they are attached is of the R configuration.

11. A compound of claim 2 where Z is hydroxy or azido, G and Z' are independently hydrogen or methyl and J is hydrogen.

12. A compound of claim 11 where B is straight or branched lower alkylene, straight or branched lower alkylenylaryl, or a direct link.

13. A compound of claim 11 where A is a divalent group selected from a straight or branched alicyclic group; a straight or branched heteroalicyclic group; aryl; or heteroaryl; all optionally substituted with substituents independently selected from amino, halogen, hydroxy, cyano, lower alkyl, lower perhaloalkyl, lower alkoxy, lower aryl, lower aryloxy, aralkyl, aralkoxy, and heteroaryl; or is a direct link.

14. A compound of claim 11 where X is hydrogen, carboxyl, carboxyalkyl, carboxyaryl, carboxyaralkyl, tetrazolo, 3H-1,2,3,5-oxythiodiazolo, thiazolidine-2-,4-diono, oxazolidin-2,4-diono, or C(W)CO$_2$E(COQ);

where E and E' are independently selected from hydrogen, lower alkyl, aryl or aralkyl;

W is hydrogen or lower alkyl;

Q is lower alkoxy, aralkoxy, aralkylamino, alkylamino, hydroxy, amino, arylamino or aryloxy.

15. A compound of claim 11 where B is straight or branched lower alkylene, straight or branched lower alkylenylaryl, or a direct link;

A is a divalent group selected from a straight or branched alicyclic group; a straight or branched heteroalicyclic group; aryl; or heteroaryl; all optionally substituted with substituents independently selected from amino, halogen, hydroxy, cyano, lower alkyl, lower perhaloalkyl, lower alkoxy, lower aryl, lower aryloxy, aralkyl, aralkoxy, and heteroaryl; or is a direct link;

X is hydrogen, carboxyl, carboxyalkyl, carboxyaryl, carboxyaralkyl, tetrazolo, 3H-1,2,3,5-oxythiodiazolo, thiazolidine-2-,4-diono, oxazolidin-2,4-diono, or C(W)CO$_2$E(COQ);

where E and E' are independently selected from hydrogen, lower alkyl, aryl or aralkyl;

W is hydrogen or lower alkyl;

Q is lower alkoxy, aralkoxy, aralkylamino, alkylamino, hydroxy, amino, arylamino or aryloxy.

16. A compound of claim 15 where X is hydrogen and A is a direct link.

17. A compound of claim 15 where X is hydrogen and A is aryl.

18. A compound of claim 15 where X is hydrogen and A is alicyclic.

19. A compound of claim 15 where A is a direct link and X is carboxyl, carboxyalkyl, carboxyaryl, carboxyaralkyl, tetrazolo, 3H-1,2,3,5-oxythiodiazolo, thiazolidine-2-,4-diono, oxazolidin-2,4-diono.

20. A compound of claim 15 where A is a direct link, and X is C(W)CO$_2$E(COQ) where E and E' are independently selected from hydrogen, lower alkyl, aryl or aralkyl;

W is hydrogen or lower alkyl;

Q is lower alkoxy, aralkoxy, alkylamino, hydroxy, amino, arylamino, aralkylamino or aryloxy.

21. A compound of claim 15 where A is not a direct link and X is carboxyl, carboxyalkyl, carboxyaryl, carboxyaralkyl, tetrazolo, 3H-1,2,3,5-oxythiodiazolo, thiazolidine-2-,4-diono, oxazolidin-2,4-diono.

22. A compound of claim 15 where B is methylene, A is 1,2-[6,6-dimethyl[3.1.1]bicyclohept-2-methylene] and X is hydrogen.

23. A compound of claim 15 where A is cycloheptylene, B is a direct link and X is hydrogen.

24. A compound of claim 15 where B is —(CH$_2$)$_4$—, A is a direct link, X is —C(W)CO$_2$E(COQ) where W is hydrogen or methyl, E is aralkyl and Q is hydroxy.

25. A compound of claim 15 where B is —(CH$_2$)$_4$—, A is a direct link, X is —C(W)CO$_2$E(COQ) where W is hydrogen or methyl, E is hydroxy, and Q is aralkylamino.

26. A compound of claim 15 where B is 1,7-[3,7-dimethyloct-6-enylene], A is a direct link and X is hydrogen.

27. A compound of claim 15 where B is lower alkylene of two to seven carbons and A is aryl.

28. A compound of claim 27 where B is lower alkyl of one to five carbons and A is phenylene.

29. A compound of claim 28 where A is 1,2-phenylene and X is methyl.

30. A compound of claim 28 where A is 1,4-phenylene and X is propoxy.

31. A compound of claim 15 where B is —(CH$_2$)$_2$—, and A is 1,3-arylene and X is carboxyl.

32. A compound of claim 15 where B is —(CH$_2$)$_2$— and A is optionally substituted naphthalene.

33. A compound of claim 15 where B is —(CH$_2$)$_2$—, A is 1,3-(2-methyl)phenylene and X is carboxyl.

34. A compound of claim 15 where B is —(CH$_2$)$_2$—, A is 1,3-naphthylene and X is carboxyl.

35. A compound of claim 15 where B is —(CH$_2$)$_2$—, A is 1,3-(5-bromo)phenylene and X is carboxyl.

36. A compound of claim 15 where B is —(CH$_2$)$_2$—, A is 2,4-thienyl and X is carboxyl.

37. A compound of claim 15 where B is 1,5-(6-arylhexylene) and X is carboxyl.

38. A compound of claim 15 where B is 1,5-(6-phenylhexylene) and X is carboxyl.

39. A compound of claim 15 where B is 1,5-(6-(3-bromophenyl)hexylene) and X is carboxyl.

40. A compound of claim 15 where B is alkyl of four to ten carbons, A is a direct link and X is hydrogen.

41. A compound of claim 15 where B is heptyl, A is a direct link and X is hydrogen.

* * * * *

UNITED STATES PATENT AND TRADEMARK OFFICE
CERTIFICATE OF CORRECTION

PATENT NO. : 5,731,432
DATED : March 24, 1998
INVENTOR(S) : Mark D. Erion et al.

It is certified that error appears in the above-identified patent and that said Letters Patent is hereby corrected as shown below:

Column 40, Line 50: After "immunosuppressive" insert --e.g.--

Column 61, Line 57: Delete "throough" and insert --through--

Column 67, Line 30, Claim 9: Delete "m" and insert --E--

Signed and Sealed this

Twenty-sixth Day of January, 1999

Attest:

*Attesting Officer*

*Acting Commissioner of Patents and Trademarks*